United States Patent
Rhyne et al.

(10) Patent No.: US 9,482,665 B2
(45) Date of Patent: Nov. 1, 2016

(54) IMMUNOASSAY STANDARDS AND MEASUREMENT OF CLINICAL BIOMARKERS USING INTRA-ASSAY CALIBRATION STANDARDS

(71) Applicant: Bristol-Myers Squibb Company, Princeton, NJ (US)

(72) Inventors: Paul Rhyne, Doylestown, PA (US); Claudio Mapelli, Plainsboro, NJ (US); Oitak Allen Wong, Princeton, NJ (US); Flora Berisha, Princeton, NJ (US); Robert John Neely, Mt. Laurel, NJ (US)

( * ) Notice: Subject to any disclaimer, the term of this patent is extended or adjusted under 35 U.S.C. 154(b) by 61 days.

(21) Appl. No.: 14/529,994

(22) Filed: Oct. 31, 2014

(65) Prior Publication Data
US 2015/0153339 A1 Jun. 4, 2015

Related U.S. Application Data

(63) Continuation of application No. 13/577,463, filed as application No. PCT/US2011/024151 on Feb. 9, 2011, now abandoned.

(60) Provisional application No. 61/302,835, filed on Feb. 9, 2010.

(51) Int. Cl.
| | |
|---|---|
| *C07K 16/28* | (2006.01) |
| *G01N 33/543* | (2006.01) |
| *G01N 33/531* | (2006.01) |
| *G01N 33/68* | (2006.01) |

(52) U.S. Cl.
CPC ......... *G01N 33/54393* (2013.01); *C07K 16/28* (2013.01); *G01N 33/531* (2013.01); *G01N 33/6896* (2013.01); *G01N 2333/4709* (2013.01)

(58) Field of Classification Search
CPC ............. C07K 16/18; G01N 33/6896; G01N 2800/2821
See application file for complete search history.

*Primary Examiner* — Shafiqul Haq
*Assistant Examiner* — Carmencita M Belei

(57) ABSTRACT

The present invention provides novel compositions and methods for creating quantitative standards to calibrate analytes. These compositions and methods enable the creation of standards and calibrators for analyzing analytes and measuring clinical biomarkers. Also provided are kits comprising the novel compositions for use in assays, for example sandwich immunoassays.

4 Claims, 36 Drawing Sheets

| Selected Bead Set # | Aβ40 peptide coupling concentration [μg/35ml] | Median Fluorescence Intensity (MFI) |
|---|---|---|
| 5 | 0 | 14 |
| 10 | 1 | 28 |
| 20 | 10 | 151 |
| 40 | 100 | 782 |
| 70 | 500 | 1944 |
| 90 | 5000 | 7869 |

FIG. 5A

| Sample | Results generated from Intra-assay $A\beta_{40}$ std curves (circles) | Results generated from $A\beta_{42}$ soluble std curves (triangles) |
|---|---|---|
| CSF-1 | 781 pg/ml | 781 pg/ml |
| CSF-2 | 213 pg/ml | 212 pg/ml |
| CSF-3 | 152 pg/ml | 150 pg/ml |
| CSF-4 | 224 pg/ml | 223 pg/ml |

FIG. 5C

IMMUNOASSAY STANDARDS AND MEASUREMENT OF CLINICAL BIOMARKERS USING INTRA-ASSAY CALIBRATION STANDARDS

This application is a continuation of U.S. application Ser. No. 13/577,463, filed Aug. 7, 2012, now pending, which is a 371 of PCT/US2011/024151, filed Feb. 9, 2011, which claims the benefit of Provisional Application No. 61/302,835, filed Feb. 9, 2010. The entire contents of the above-identified applications are hereby incorporated by reference.

FIELD OF THE INVENTION

Background of the Invention

Amyloid Beta (Aβ) peptides are generated from the cleavage of Amyloid Precursor Protein (APP) via beta secretase and gamma secretase enzymatic complexes (Wolfe, Biochemistry, 45:7931-7939 (2006)). Beta secretase generates the N-terminal ends of these amyloid peptides and gamma secretase generates the C-terminal ends (Wolfe, Biochemistry, 45:7931-7939 (2006)). Several species of peptides are subsequently generated, typically ranging from 38 to 42 amino acids in length depending on where the gamma secretase cleaves the APP. Aβ peptides have an extracellular domain (amino acids 1-28) and a transmembrane region (amino acids 29-42) that is embedded in the lipid bilayer. Amyloid peptides that are 42 amino acids long ($A\beta_{42}$) are believed to be the putative neurotoxic species, either alone or as aggregates. These aggregates are suspected to contribute to the neurodegeneration of the brain resulting in Alzheimer's disease and dementia. The hypothesis that $A\beta_{42}$ contributes to clinical dementias is called the amyloid cascade hypothesis as described by Hardy et al. (Science, 256: 184-185 (1992)).

One of the characteristics of the Aβ peptides is the ability to self-assemble into oligomers at physiological concentrations (Burdick et al, Journal of Biological Chemistry, 267: 546-554 (1992); Cerf et al, Biochemical Journal, 421:415-423 (2009).). The $A\beta_{42}$ species is more prone to forming oligomers as compared to the $A\beta_{40}$ and $A\beta_{38}$ species. The mechanism of oligomer formation has been shown to originate from a small, five amino acid region located at amino acids 16 to 20 (KLVFF) which mediates the binding of Aβ peptides in an anti-parallel manner. This small region has thus been termed the "aggregation domain" (Tjernberg et al, Journal of Biological Chemistry, 271:8545-8548 (1996)). Aβ peptide aggregates assemble rapidly (i.e., within minutes) under certain conditions especially at lower pH ranges, with slightly slower kinetics at neutral or higher pH (Burdick et al, Journal of Biological Chemistry, 267:546-554 (1992)). The aggregates are poorly soluble in aqueous solutions, especially in the presence of salts. The C-terminal ends of the Aβ peptides fold back over the core of the dimer via salt bridges thereby increasing their hydrophobicity and promoting further polymerization of the peptides into filaments or fibrils. The additional two C-terminal residues in the $A\beta_{42}$ species provides increased hydrophobicity in comparison to the other Aβ species (Kim et al, Journal of Biological Chemistry, 280:35069-35076 (2005)).

Clinical data suggests that the degree of dementia and cognitive decline has a higher correlation with $A\beta_{42}$ concentration than either the $A\beta_{40}$ or $A\beta_{38}$ species. This observation, in conjunction with the rapid aggregation properties of $A\beta_{42}$, has led to the hypothesis that inhibition of $A\beta_{42}$ aggregation may have clinical benefits. There have been numerous studies showing different mechanisms that can be used to inhibit the formation of $A\beta_{42}$ aggregates. Tjernberg et al. (Journal of Biological Chemistry, 271: 8545-8548 (1996)) showed that peptides comprising the aggregation domain bind well to Aβ peptides and inhibit the formation of aggregates. Several other molecules that bind to the aggregation domain have also been shown to inhibit amyloid peptide aggregation (Martharu et al, Journal of Neurological Sciences, 280:49-58 (2009); Kim et al, Biochemical and Biophysical Research Communications, 303:576-279 (2003)). Substitution of amino acids in the aggregation core domain or the deletion of the entire aggregation domain also prevents Aβ peptide aggregation and fibril formation (Tjernberg et al, Journal of Biological Chemistry, 274: 12619-12625 (1999)). In addition, various drugs have been designed to inhibit gamma secretase activity in order to lower the amount of $A\beta_{42}$ and related peptide species. The usefulness of these approaches in the clinic is currently under investigation.

In order to assess the effectiveness of a molecule to inhibit the generation of $A\beta_{42}$ or to prevent its aggregation, it is necessary to measure the amount of $A\beta_{42}$ accurately. There are several techniques that are used to detect and quantitate $A\beta_{42}$ in biological samples including both immunoassays (Olsson et al, Clinical Chemistry, 51:336-345 (2005); Verwey et al, Journal of Immunological Methods, 348:57-66 (2009); Sjogren et al, Journal of Neural Transmission, 107:563-679 (2000)) and mass spectrometry (MS) based methods (Cantone et al, Journal of Neuroscience Methods, 180:255-260 (2009); Journal of Mass Spectrometry, 40: 142-145 (2005)). The MS based methods, including those of MALDI-TOF and SELDI-TOF along with liquid chromatography prepared mass spectrometry, are able to detect many of the amyloid beta species in a biological sample, but do not presently provide sufficient quantitative values that are needed for measuring $A\beta_{42}$ in clinical samples.

Immunoassay methods are based on a double sandwich immunoassay that comprises one antibody that is specific to the N-terminus and a second antibody that is highly specific for the $A\beta_{42}$ C-terminus (i.e., does not recognize other Aβ peptide species). There are two basic versions of the immunoassays. The first version captures Aβ peptides in biological samples via a solid surface immobilized N-terminal region specific antibody. The $A\beta_{42}$ specific antibody carrying a tag is added to the immunoassay in order to complete the antibody sandwich. The second version captures Aβ peptides in biological samples via an $A\beta_{42}$ C-terminal region specific antibody immobilized on a solid surface. The N-terminal region specific antibody carrying a tag is added to the immunoassay. In either version, the tag incorporated via the second antibody enables the detection of the complete complex. These assays are made quantitative by the use of $A\beta_{42}$ reference standards, which are added in lieu of biological samples. The resulting signal measured from the reference standards are used to generate a standard curve which is subsequently used to quantify the amount of $A\beta_{42}$ in the biological samples.

Until now, the use of $A\beta_{42}$ reference standards in immunoassays has relied on synthetic, full length $A\beta_{42}$ peptides which are typically generated with minimal difficulty. However, these peptides have strong hydrophobic properties and, therefore, are not soluble in aqueous solutions. In addition, the storage and use of $A\beta_{42}$ as reference standards presents many issues. As discussed, $A\beta_{42}$ forms aggregates rapidly and this formation occurs more readily at room temperatures and neutral pH. Long term storage at low temperatures (below −20° C.) and low pH helps to minimize aggregation during storage but it does not prevent it. Reconstitution of $A\beta_{42}$ in buffers that are amenable to immunoassays can also prove difficult. These solutions are almost always aqueous, buffered at a neutral pH, contain salts, and used at room temperature; all the conditions that accelerate $A\beta_{42}$ aggregation. $A\beta_{42}$ peptides that have aggregated are not useful as reference standards in immunoassays because of the insoluble precipitates and non-uniformity in both size and availability to be recognized by either detection or capture antibodies.

Thus, the present invention fulfills a need in the art by providing methods useful for generating an $A\beta_{42}$ peptide or protein construct and compositions thereof that can be used as a reference standard or calibrator in an immunoassay or other format to measure the abundance of $A\beta_{42}$ peptide accurately in a fluid or tissue extract sample. Specifically, the compositions and methods of the present invention are aimed at creating non-aggregating peptide reference standards for $A\beta_{42}$ for use in immunoassay formats. The compositions and methods described herein have a broad applicability to many other peptides that are difficult to measure and quantitate.

BRIEF SUMMARY OF THE INVENTION

In one aspect, the invention provides a composition comprising an N-terminal immunoreactive region, a C-terminal immunoreactive region and a linker region. In another aspect, the invention provides a composition comprising an N-terminal immunoreactive region, a C-terminal immunoreactive region and a linker region, wherein the composition is used as a reference standard in an immunoassay. In one embodiment, the immunoassay is selected from the group consisting of a sandwich immunoassay, a single antibody assay, a double sandwich immunoassay and a competition assay. In another embodiment, the composition is selected from the group consisting of a protein, a peptide, a fragment and a modified protein. In one embodiment, the N-terminal immunoreactive region binds $A\beta_{42}$; $A\beta_{40}$, $A\beta_{38}$, tau or insulin growth factor receptor 1. In another embodiment, the C-terminal immunoreactive region binds $A\beta_{42}$; $A\beta_{40}$, $A\beta_{38}$, tau or insulin growth factor receptor 1. In another embodiment, the linker region is a non-immunoreactive domain. In another embodiment, the linker region comprises a linker selected from the group consisting of polyethylene glycol, a glutamine residue, an alanine residue, a lysine residue, a lipid, a globular protein, a nucleic acid (including but not limited to DNA, RNA and PNA) and an alkyl chain.

In another aspect, the invention provides an isolated peptide molecule having an amino acid sequence of SEQ ID NO: 1, 2, 3, 4, 5, 6, 7, 8, 9, 10, 11, 12, 13, 14, 15, 17, 19, 21, 22, 23, 24, 25, 26 or 27.

In another aspect, the invention provides a method of measuring the quantity of an analyte in a biological sample, the method comprising: attaching a reference standard to at least two beads thereby forming a first bead set and a second bead set, wherein the reference standard comprises an epitope recognized by a first detection antibody and wherein each bead set comprises a different concentration of the reference standard; attaching a capture antibody specific to the analyte to a third bead set; mixing all of the bead sets together to form a suspension array; applying the biological sample to the suspension array whereby the analyte binds to the capture antibody on the third bead set; adding a first detection antibody to the suspension array, wherein the first detection antibody binds the reference standard and analyte bound to the capture antibody; measuring a first signal from the first detection antibody bound to the reference standard in the first bead set; measuring a second signal from the first detection antibody bound to the reference standard in the second bead set; generating a standard curve based upon the first and second signals; and quantitating the amount of the analyte in the third bead set by measuring a third signal from the first detection antibody and comparing the third signal to the first and second signal measurements on the standard curve.

In one embodiment, the reference standard comprises a composition comprising an N-terminal immunoreactive region, a C-terminal immunoreactive region and a linker region. In another embodiment, the reference standard comprises a peptide or modified peptide having an amino acid sequence of SEQ ID NO: 1, 2, 3, 4, 5, 6, 7, 8, 9, 10, 11, 12, 13, 14, 15, 17, 19, 21, 22, 23, 24, 25, 26 or 27.

In another embodiment, the biological sample is selected from the group consisting of blood, serum, plasma, peripheral blood mononuclear cells, peripheral blood lymphocytes, tissue, cerebrospinal fluid and cells. In another embodiment, the analyte is selected from the group consisting of $A\beta_{42}$, $A\beta_{40}$, $A\beta_{38}$, tau or insulin growth factor receptor 1.

In another embodiment, the method is performed in a multi-well plate, nitrocellulose filter, glass fiber or on a glass slide. In another embodiment, the first signal and second signal is a signal selected from the group consisting of phycoerythrin, alexa 532, streptavidin-phycoerythrin and streptavidin-Alexa 532. In another embodiment, the reference standard is covalently attached to the bead. In another embodiment, the capture antibody is covalently attached to the bead. In another embodiment, the covalent attachment is a carbodimide bond.

In another aspect, the present invention provides a kit for conducting an immunoassay to detect $A\beta_{42}$ peptide, the kit comprising a composition of the present invention.

BRIEF DESCRIPTION OF THE TABLES

Table 1 shows the desirable physical properties of the $A\beta$ peptides and the tests used to measure those properties.

Table 2 shows $A\beta_{42}$ peptide and modified peptide sequences and descriptions.

Table 3 shows tau peptide and modified peptide sequences and descriptions.

Table 4 shows the measured concentration of $A\beta_{42}$ peptide in three human cerebrospinal (CSF) samples.

Table 5 shows a list of the novel $A\beta$ peptides that were characterized.

Table 6 shows a summary of dynamic light scattering (DLS) data.

BRIEF DESCRIPTION OF THE FIGURES

FIG. 3A shows a calibration curve from modified standard 2 (SEQ ID NO:2) and 4 (SEQ ID NO:4).

FIG. 3B shows a calibration curve from modified standard 12 (SEQ ID NO: 12) and 13 (SEQ ID NO: 13).

FIG. 3C shows a calibration curve from modified standard 14 (SEQ ID NO: 14) and 6 (SEQ ID NO:6).

FIG. 5A shows the measured Median Fluorescence Intensity (MFI) of 6 different Luminex bead sets covalently coupled with different concentrations of Aβ 1-40 peptide (SEQ ID NO: 15).

FIG. 5C shows the measured Aβ$_{42}$ peptides in human CSF samples using either a calibration curve generated from soluble Aβ$_{42}$ peptides or from the intra-assay Aβ$_{40}$ standards.

DETAILED DESCRIPTION OF THE INVENTION

Figure 1:
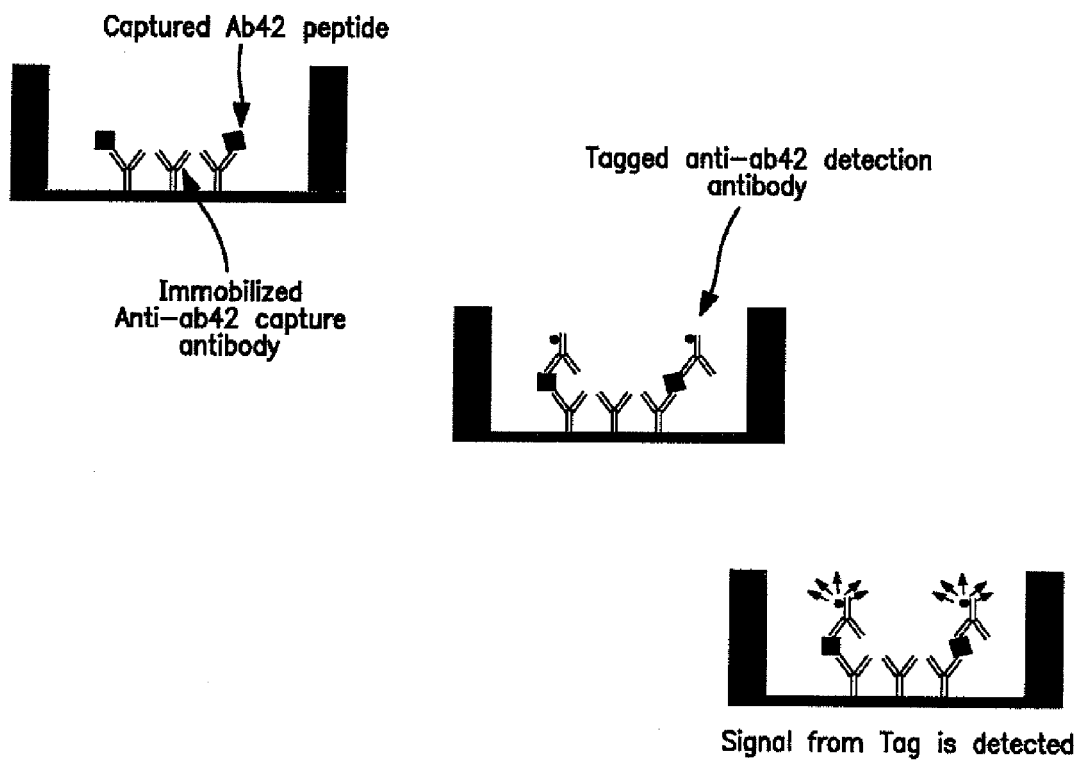
FIG. 1 shows a schematic of a two-sided or sandwich soluble standard.

The present invention may be understood more readily by reference to the following detailed description of the preferred embodiments of the invention and the Examples included herein.

This invention relates to novel compositions and methods that can be used as reference standards and calibrators in order to measure clinical biomarkers in an immunoassay. This invention also relates to methods of using the compositions and kits comprising the compositions. Specifically, the compositions and methods of the present invention are aimed at creating non-aggregating peptide reference standards for Aβ$_{42}$ or tau for use in immunoassay formats.

This invention also relates to kits comprising the compositions of the invention.

DEFINITIONS

As used herein, the term "Aβ" refers to amyloid beta.

As used herein, the term "Aβ$_{42}$" refers to Amyloid Beta 1-42. "Aβ$_{42}$" refers to a 42 amino acid length peptide that has an amino acid sequence as noted in Table 2, SEQ ID O: 1.

As used herein, the term "Aβ$_{38}$" refers to Amyloid Beta 1-38. "Aβ$_{38}$" refers to a 38 amino acid length peptide that has the sequence DAEFRHDSGYEVHHQKLVFFAEDVGSNKGAIIGLMVGG (SEQ ID NO: 17).

As used herein, the term "Aβ$_{40}$" refers to Amyloid Beta 1-40. "Aβ$_{40}$" refers to a 40 amino acid length peptide that has the sequence as noted in Table 2, SEQ ID NO: 15.

As used herein, the term "tau" refers to the native tau protein corresponding to the amino acid sequence as noted in Table 3, SEQ ID NO:20.

As used herein, the term "antibody" is used in the broadest sense, and specifically covers monoclonal antibodies (including full length monoclonal antibodies), polyclonal antibodies, multispecific antibodies (i.e., bispecific antibodies), and antibody fragments (i.e., Fab, F(ab').sub.2 and Fv) so long as they exhibit binding activity or affinity for a selected antigen. "Antibody" can also refer to an antibody or antibody fragments hanging or fused to carrier proteins/organisms such as phage or other display carriers that have the same properties as isolated antibodies.

As used herein, the term "isolated", as used herein with reference to the subject proteins and protein complexes, refers to a preparation of protein or protein complex that is essentially free from contaminating proteins that normally would be present with the protein or complex (i.e., in the cellular milieu in which the protein or complex is found endogenously). Thus, an isolated protein complex is isolated from cellular components that normally would "contaminate" or interfere with the study of the complex in isolation, for instance while screening for modulators thereof. It is to be understood, however, that such an "isolated" complex may incorporate other proteins the modulation of which, by the subject protein or protein complex, is being investigated.

As used herein, the term "isolated" as also used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

As used herein, the term "nucleic acid" refers to polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide, "Nucleic acid" can also refer to a peptide nucleic acid "PNA" or an artificially synthesized DNA or RNA.

As used herein, the terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. As used herein, the term "modified peptide" refers a peptide that has been modified relative to the native sequence of that peptide. For example, a modification may include the removal of a deleterious domain or the addition of a linker within the native peptide sequence.

As used herein, the term "binding" refers to a direct association between two molecules, due to, for example, covalent, electrostatic, hydrophobic, ionic and/or hydrogen-bond interactions under physiological conditions. Likewise, "complex formation," between two or more polypeptides, refers to a direct association between polypeptides, due to, for example, covalent, electrostatic, hydrophobic, ionic and/ or hydrogen-bond interactions under physiological conditions.

As used herein, the term "domain" refers to a region of a protein that comprises a particular structure and/or performs a particular function (i.e., aggregation domain, "phosphorylation domain"). The term "aggregation domain" as used herein refers to a five amino acid region located at amino acids 16 to 20 (KLVFF (SEQ ID NO: 18)) which mediates the binding of Aβ peptides in an anti-parallel manner.

As used herein, the term "immunoreactive domain" refers to a region of a protein that comprises a particular amino acid sequence that can be recognized by an antibody. This region includes amino acid sequences that contain modifications such as glycosylation, methylation, phosphorylation or any other post-translational modification known to one of ordinary skill in the art. An "immunoreactive" domain would also include two or more regions of a protein that are in close proximity to one another in the proteins native folded state, which together comprise an antibody binding site.

As used herein, the term "immunoassay" as used herein refers to a biochemical test that utilizes one or more antibodies to measure the presence or concentration of an analyte in a biological matrix. This assay can produce a measurable signal in response to a specific binding of an antibody to an immunoreactive domain of a specific protein or peptide.

Reference Standards

In one aspect, this invention relates to compositions that can be used as reference standards and calibrators in order to measure clinical biomarkers. In one embodiment, the reference standard comprises a peptide. The peptide may be a modified peptide. The modified peptide may comprise a linker, a deletion or substitution in a non-immunoreactive domain. In another embodiment, the non-immunoreactive domain is an aggregation domain or phosphorylation domain.

Alterations in the Aggregation or Non-Immunoreactive Domain

In one aspect, the present invention provides modified peptides which can be used as reference standards. There are known domains or amino-acid sequences which lead to the self-aggregation and non-specific interactions of sticky peptides like $A\beta_{42}$ with itself and other molecules. As such, it is possible to construct standards or calibrators which lack these deleterious domains. The present invention provides several ways in which to modify the peptides in order to remove the deleterious domains. In one embodiment, the amino acids comprising the deleterious domains are deleted from the amino acid sequence and the N-terminal immunoreactive domain is connected to the C-terminal immunoreactive domain, lacking the central 17-20 amino acid sequence as well as various lengths of adjacent C-terminal peptide in the case of $A\beta_{42}$. Examples of $A\beta_{42}$ peptides with the central domains deleted are shown in Table 2, SEQ ID NOs:2, 3, and 4. In another embodiment, the central aggregation domain plus the adjacent amino acids are replaced with a linker or spacer consisting of many different types of matter.

In another embodiment, amino acids that do not aggregate are contemplated as the linker. In one embodiment, the amino acids that do not aggregate are in the form of a hydrophilic spacer or linker of the amino acid sequence or form EERP, shown with both the C-terminal 37-42 sequences of $A\beta_{42}$ (SEQ ID NO:5) and the C-terminal 32-42 portions of $A\beta_{42}$ (SEQ ID NO: 6). In another embodiment, the $A\beta_{42}$ peptide includes a longer hydrophilic linker, for example the amino acid sequence DREPNR (SEQ ID NO: 16), with both the C-terminal 37-42 (SEQ ID NO:7) and C-terminal 32-42 (SEQ ID NO:8) portions of $A\beta_{42}$.

In yet another embodiment, a series of charged residues are used in the form of the linker between the N-terminal and C-terminal immunoreactive domains. In another embodiment, a linker is created consisting of an integer number m Lysine residues (SEQ ID NO:9) or integer number n Glutamic acid residues (SEQ ID NO: 10). In another embodiment, a string of neutral residues is used as a linker. In another embodiment, a construct consisting of an integer number p alanine residues (SEQ ID NO: 11) is contemplated.

In another embodiment of the present invention, various forms of polyethylene glycol (PEG) are used as a linker. In a preferred embodiment, PEG-6atom and PEG-20atom are used with various C-terminal portions (SEQ ID NOs: 12-14). In another embodiment, any polymer with chemistry able to couple to amino acid residues is used as a linker or spacer. This polymer includes those of a linear form as well as those of known branched topology, like dendrimers and branched co-polymers, to simulate the immunoreactivity of oligomers of $A\beta_{42}$ and other similar sticky or self aggregating molecules.

Phosphorylated regions of Tau may also be used to generate modified peptides that may be used as reference standards. The abnormally hyperphosphorylated tau is associated with neurofibrillary tangles. There are multiple phosphorylation sites of Tau; each of them has different effect on its biological function. Measurement of phosphorylated Tau at Ser202/Thr1 81/Thr212/Thr231 or Ser262 may help to understand which one correlates with cognitive decline in MCI subject. Thus, in another embodiment, a modified tau peptide is contemplated as the reference standard. Examples of modified tau peptides are shown in Table 3.

In another embodiment, the linker comprises any one of the following molecules: lipids, globular proteins, nucleic acids (including but not limited to DNA, RNA and PNA), alkyl chains, or any other linkage that adds to the stability of the two immune epitopes of interest in the immunoassay. In another embodiment, the bond between the peptide backbone and linker comprises a covalent bond, avidin-biotin complex or any other stable bond. In another embodiment, the construct does not lead to self aggregation or non specific absorption to laboratory plastics, in particular polypropylene, polystyrene, polycarbon and other laboratory plastic resins of which pipette tips, tubes, plates and other vessels which hold fluids in which the analyte of interest can be measured.

In another embodiment, the novel $A\beta_{42}$ or tau immunoassay standards or calibrators require the presence of the N-terminal epitope that is recognized by the N-terminal specific antibody. There are many $A\beta_{42}$ N-terminal binding antibodies that are known in the art. For example, 6E10 is known to recognize the $A_{3-8}$ epitope whereas 3D6 is known to recognize the N-terminal epitope of Aβ. An overlapping epitope may be designed to allow a selection of several N-terminal specific antibodies to be used, depending on the immunoassay requirements and detection system.

In another embodiment, the novel $A\beta_{42}$ immunoassay standards or calibrators require the presence of the C-terminal epitope that is recognized by the C-terminal $A\beta_{42}$ specific antibody. Examples of well characterized C-terminal $A\beta_{42}$ neo-epitope antibodies include G2-1 1 (from Heidelberg University), 2 IF 12 (from Athena Diagnostics), 4D7A3 (from Innogenetics), and 12F4 (from Covance, formerly Signet). An overlapping c-terminal epitope may be designed to allow a selection of several C-terminal $A\beta_{42}$ specific antibodies to be used, depending on the immunoassay requirements and detection system.

In another embodiment, any N-terminal binding, C-terminal binding or phosphorylated tau binding antibody known to one of ordinary skill in the art may be used herein.

The invention also relates to methods for generating a peptide or protein construct and compositions thereof that can be used as a reference standard or calibrator in an immunoassay to measure the abundance of a peptide accurately in a fluid or tissue extract sample. An immunoassay often requires biologically specific capture reagents, such as antibodies, to capture the analytes or biomarkers of interest. Antibodies can be produced by methods well known in the art, i.e., by immunizing animals with the biomarkers as antigens. Biomarkers can be isolated from samples based on their binding characteristics. Alternatively, if the amino acid sequence of a polypeptide biomarker is known, the polypeptide can be synthesized and used to generate antibodies by methods well known in the art. Examples of biomarkers include Aβ peptides and tau.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an mass spectrometry (MS) probe, such as a pre-activated PROTEINCHIP® array. The biomarker is then specifically captured on the biochip through this reagent, and the captured biomarker is detected by mass spectrometry.

Thus, in one aspect, the invention relates to methods of measuring the clinical markers with the reference standards of the invention. In one embodiment, the reference standard is measured by immunoassay. In another embodiment, the immunoassay is a sandwich immunoassay. In another embodiment, the immunoassay is a single antibody immunoassay, often run in a competitive or "competition" mode for immunoreactive binding sites. In yet another embodiment, the immunoassay is a double sandwich immunoassay or enzyme linked immunosorbant assay (ELISA).

In a preferred embodiment, the method of measuring the clinical markers is by using an immunoassay comprising the steps of attaching a reference standard to at least two beads thereby forming a first bead set and a second bead set, wherein the reference standard comprises an epitope recognized by a first detection antibody and wherein each bead set comprises a different concentration of the reference standard; attaching a capture antibody specific to the analyte to a third bead set; mixing all of the bead sets together to form a suspension array; applying the biological sample to the suspension array whereby the analyte binds to the capture antibody on the third bead set; adding a first detection antibody to the suspension array, wherein the first detection antibody binds the reference standard and analyte bound to the capture antibody; measuring a first signal from the first detection antibody bound to the reference standard in the first bead set; measuring a second signal from the first detection antibody bound to the reference standard in the second bead set; generating a standard curve based upon the first and second signals; and quantitating the amount of the analyte in the third bead set by measuring a third signal from the first detection antibody and comparing the third signal to the first and second signal measurements on the standard curve. It is understood without limitation to the present invention that a bead set could be replaced by any other solid phase in which multiplexed information can be measured independently in a particular detection technology or instrument.

In one embodiment, the reference standard comprises a composition described herein. In another embodiment, the biological sample is selected from the group consisting of blood, serum, plasma, peripheral blood mononuclear cells, peripheral blood lymphocytes tissue, cerebrospinal fluid and cells. In yet another embodiment, the analyte is $A\beta_{42}$, $A\beta_{40}$, $A\beta_{38}$, tau or insulin growth factor receptor 1.

The analyte and/or reference standard may be bound to a variety of surface. A surface could be any solid phase surface to which an antibody or reference standard can be immobilized by covalent linkage, passive absorbance, biotin-strepavidin or any other linkage known to one of ordinary skill in the art. For example, the surface may be a bead, plate, slides, fiber, surface plamon resonance sensors or any solid surface.

In another embodiment, the method is performed in a multi-well plate, nitrocellulose filter or on a glass slide. In another embodiment, the first and second signals are detected by fluorescence. For example, the first signal and second signal may be a signal selected from the group consisting of phycoerythrin, alexa 532, streptavidin-phycoerythrin and streptavidin-Alexa 532. In another embodiment, the signal is detected by enzymatic activity (i.e., horseradish peroxidase or alkaline phosphatase), chemiluminescence, radioactivity, infra-red emission, fluorescence resonance energy transfer (FRET) or any other method known to one of ordinary skill in the art.

In another aspect, the invention comprises a kit for conducting an immunoassay to detect an $A\beta_{42}$ or tau peptide, the kit comprising a reference standard of the invention.

Performance Comparison of Novel Immunoassay Standard or Calibrator to Native $A\beta_{42}$ The performance of novel immunoassay standards or calibrators should have comparable performance to the native $A\beta_{42}$ in an immunoassay. Native full length $A\beta_{42}$ peptides may be synthesized using standard solid phase techniques or they may be purchased commercially from a number of vendors as a catalog item (Anaspec Inc., American Peptide Company, or Invitrogen Inc.). Standard methods can be used to verify the abundance of the full length construction from truncated species using mass spectrometry techniques such as amino acid analysis that are well known in the field (Kanu et al, Journal of Mass Spectrometry, 43: 1-22 (2008); Bernstein et al, Journal of American Chemical Society, 127:2075-2084 (2005); Li et al, Encyclopedia of Analytical Chemistry, Meyers, R. A., ed., John Wiley & Sons Ltd. (2009)).

By way of example, Table 1 lists the desirable physical properties of $A\beta_{42}$ peptides and the various methods used to test these properties. These methods can be employed to determine if the properties of the reference standard are comparable to those of the native $A\beta_{42}$ peptide.

TABLE 1

| Property | Test | Target Range | Reference |
|---|---|---|---|
| Solubility | SDS-PAGE | Greater than 90% monomeric form | Analy. Biochem., 316: 223-231 (2003) |
| | Dynamic light scattering | Less than 5% aggregated peptides | Meth. Enzymology, 309: 429-459 (1999); J. Biol. Chem., |

TABLE 1-continued

| Property | Test | Target Range | Reference |
|---|---|---|---|
| | | | 274: 25945-25952 (1999) |
| Non-specific adsorption | Spike recovery into CSF or buffer Aβ$_{42}$ immunoassay | Recovery between 80 and 120% | Aβ Immunoassay Olsson et al., *Clinical Chemistry*, 51: 336-345 (2005) |
| Aggregation | SDS-PAGE Western blotting | Greater than 90% monomeric form | PNAS, 100: 330-335 (2003); *Analy. Biochem.*, 316: 223-231 (2003) |
| | Thioflavin T assay | Greater than 90% monomeric form | *Meth. Enzymology*, 309: 274-284 (1999) |
| Fibril information | Microscopy (transmission electron microscopy, optical, Microscopy (optical, atomic force) | Minimal levels of observable oligomers or fibrils | *Protein Pep. Letters*, 13: 261-270 (2006); *J. Am. Chem. Soc.*, 125: 15359-15365 (2003) |
| Stability at 25° C., −20° C., and −80° C. | Less than 20% CV loss of signal compared to freshly prepared Aβ$_{42}$ Via Aβ$_{42}$ immunoassay | 2 hrs 25° C. 3 months −20° C., 6 months −80° C. | Olsson et al., *Clinical Chemistry*, 51: 336-345 (2005); Verwey et al., *Journal of Immunological Methods*, 348: 57-66 (2009) |

Use of Modified Reference Standards or Calibrators in Antibody Based Immunoassays In another aspect of the present invention, the modified reference standard is used in a single antibody based assay. In one embodiment, immunoassays containing a single antibody can be used to measure Aβ$_{42}$ or tau in a biological sample by a competition immunoassay. A single antibody specific to Aβ$_{42}$ or tau is immobilized to a solid surface such as the well of a microtiter plate, a bead, or other immunoassay relevant surface. The antibody may be covalently linked via many different methods such as EDC mediated linkage of carboxyl and amine groups, or via passive absorbance or through a Protein A or Protein G interface. An Aβ$_{42}$ or tau competitor is then generated from an Aβ$_{42}$ or tau standard or calibrator containing the full length Aβ$_{42}$ or tau peptide or a modified version that retains the epitope of the capture antibody. The Aβ$_{42}$ or tau competitor is used to generate competition between the native Aβ$_{42}$ or tau in the biological sample and the binding site (paratope) on the immobilized antibody. A paratope is a term used to describe the binding region on the antibody that recognizes the epitope or immunoreactive domain on the analyte. The Aβ$_{42}$ or tau competitor is tagged for detection purposes. In one embodiment, the tag is an enzyme such as horseradish peroxidase or alkaline phosphatase. In another embodiment, the tag is a fluorescein such as phycoerythrin. In yet another embodiment, the tag is another tag such as biotin or ruthenium. In yet another embodiment, the tag is a nucleic acid such as DNA, R A or PNA, where by detection of the antibody is quantitated using sensitive technology to detect the nucleic acid flag, such as Polymerase Chain Reaction (PCR). A single concentration of the Aβ$_{42}$ or tau competitor is used in the assay and would be determined based on the ability to compete with the natural levels of Aβ$_{42}$ or tau found in biological samples.

In another embodiment, the assay is made quantitative by establishing a calibration curve. In another embodiment, quantitation is performed by making a set of Aβ$_{42}$ or tau standards or calibrators that are either the full length Aβ$_{42}$ or tau peptide or a modified version that retains the epitope of the capture antibody. These untagged standards or calibrators are prepared in either buffer or a biological matrix that does not contain Aβ$_{42}$ or tau. In one embodiment, the calibration curve is established by mixing one of concentrations of the untagged standards or calibrators with the tagged Aβ$_{42}$ or tau competitor to the immobilized antibody. The resulting signal value from each tested concentration of untagged standard or calibrator is used to generate a standard curve; plotting the concentration of the untagged Aβ$_{42}$ or tau standards or calibrators versus the resulting signal values. Once a standard quantitative curve is established, an assay is used to determine the levels of native Aβ$_{42}$ or tau in biological samples by mixing the tagged Aβ$_{42}$ or tau competitor at the same fixed concentration with the biological sample. The resulting signal value is plotted on the standard curve to determine the level of Aβ$_{42}$ or tau in the biological sample.

In another aspect of the present invention, the modified reference standard is used in a sandwich based immunoassay.

Use of Modified Standards or Calibrators in Intra-Assay Reference Standard Based Immunoassays In another aspect of the present invention, Aβ$_{42}$ or tau peptides are incorporated into an intra-assay calibration system. In this approach, a multiplex immunoassay format such as the Luminex bead based system or the Meso-Scale Discovery ECL plate based system could be used. Peptides containing amino acid residues that encompass the antibody binding epitope of the detection antibody are generated. In one embodiment, these peptides include modifications that enable them to be covalently coupled to a solid phase or modifications that increase their solubility and use in aqueous immunoassays. These peptides are immobilized at different concentrations to the relevant solid phase as defined by multiplexed immunoassay systems, in order to create a set of well defined standards from which to create a standard curve.

The measurement of soluble biomarkers in clinical samples is often done using double antibody sandwich assays. These assays require two antibodies that are specific to the biomarker and a technology in which to detect the captured biomarker using the second "reporter" or "detection" antibody. Protein reference standards are required in order to make the assay quantitative. These standards are often in the form of recombinant proteins; however, they may also be obtained from biological samples. Traditional assay formats for these assays include ELISA techniques that provide quantitation suitable for the analysis of clinical samples. However, they are often limited to one biomarker assay per well. Newer technologies have been developed that allow multiple biomarkers to be analyzed in a single well or reaction vessel. Some of the multiplexed technologies utilize antibodies spotted onto a solid surface such as glass slides or specialized microtiter plates. Another approach is via suspension arrays where the antibodies are bound to latex beads which are mixed together in solution to form the array.

In one embodiment, suspension array technology is used. In another embodiment, the suspension array technology is the Luminex xMAP technology. Luminex xMAP technology uses latex beads that contain a ratio of two fluorescent dyes. Different bead 'sets' are created by altering the ratio of these two dyes. The beads are mixed together to form a suspension array. The bead mixture is analyzed by an instrument that identifies each bead by the fluorescence ratio as it passes in front of a laser. These bead sets have different modifications on their surface that are used for the covalent attachment of molecules such as proteins, peptides, antibodies, etc. This allows assay to be performed on the surface of these beads. Assays are quantitated through the incorporation of a third fluorescent label such as phycoerythrin to a reporter antibody directed at the analytes of interest. A second laser in the instrument measures the fluorescence of this reporter label as the beads move through the instrument.

EXAMPLES

Example 1

Sandwich Based Assay That can be Used to Measure $A\beta_{42}$

A schematic of a two-sided or sandwich soluble standard is shown in FIG. 1. Briefly, capture antibodies specific to the C-terminus of $A\beta_{42}$ were immobilized to a solid surface. A biological sample was added thereby allowing $A\beta_{42}$ to be captured by the immobilized antibody. A second tagged detection antibody was added that was specific to the N-terminus of the $A\beta_{42}$. The measured signal generated by the tagged detection antibody was used for quantitation.

Figure 2:
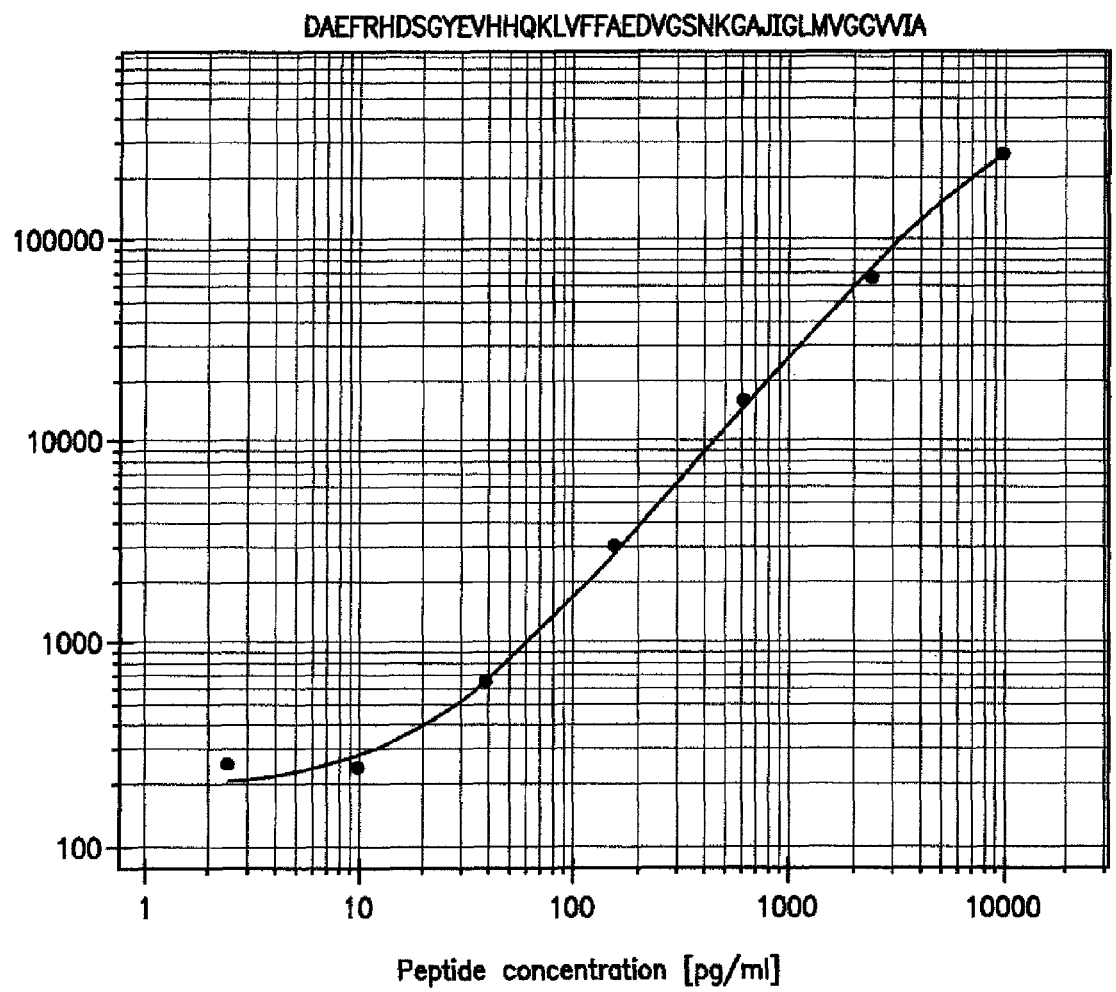
FIG. 2 shows a calibration curve from an exemplary $A\beta_{42}$ sandwich immunoassay.
Figure 3A:
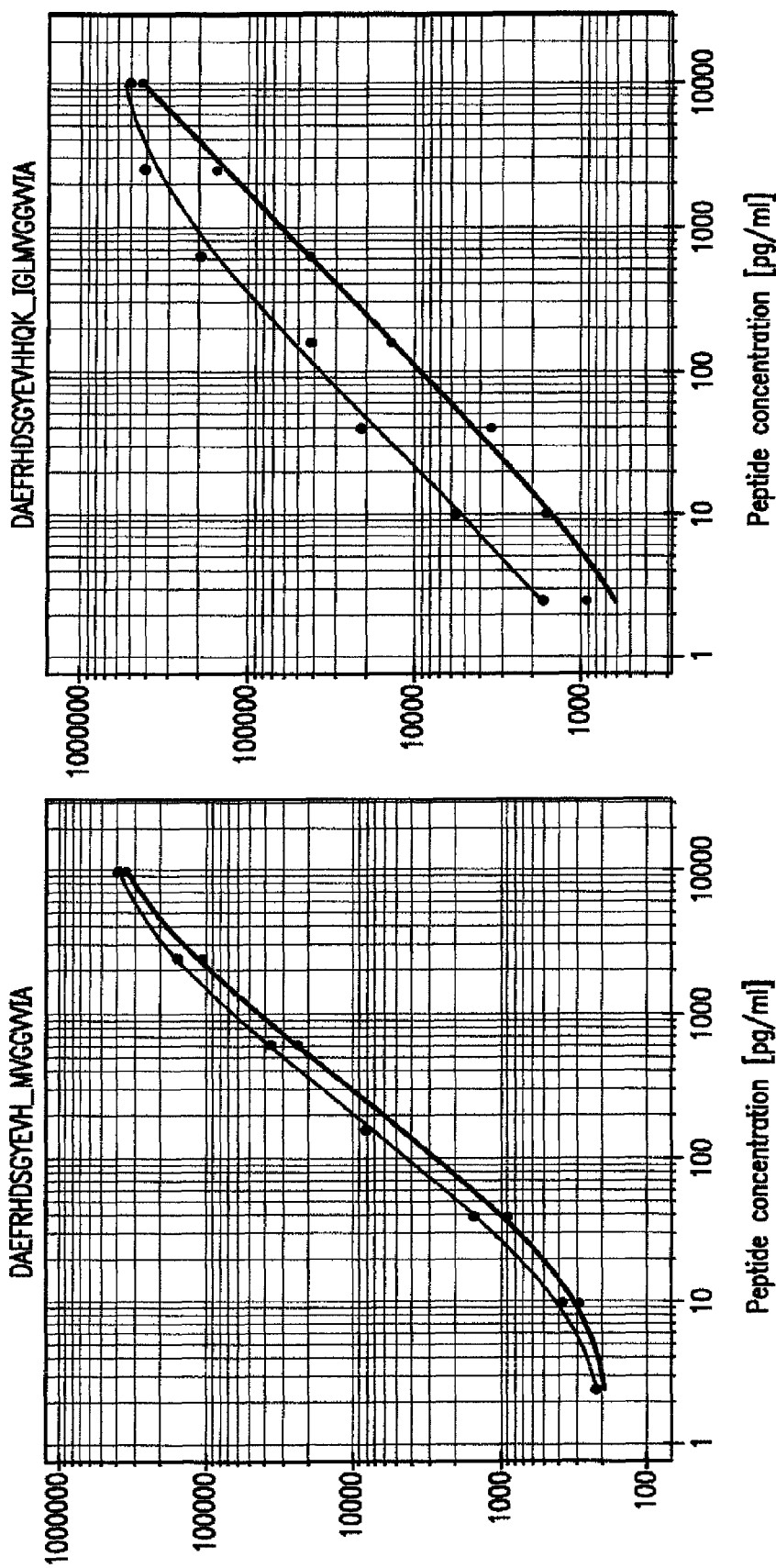
FIGS. 3A-C show an exemplary $A\beta_{42}$ sandwich assay using modified $A\beta_{42}$ peptide standards.
Figure 3B:
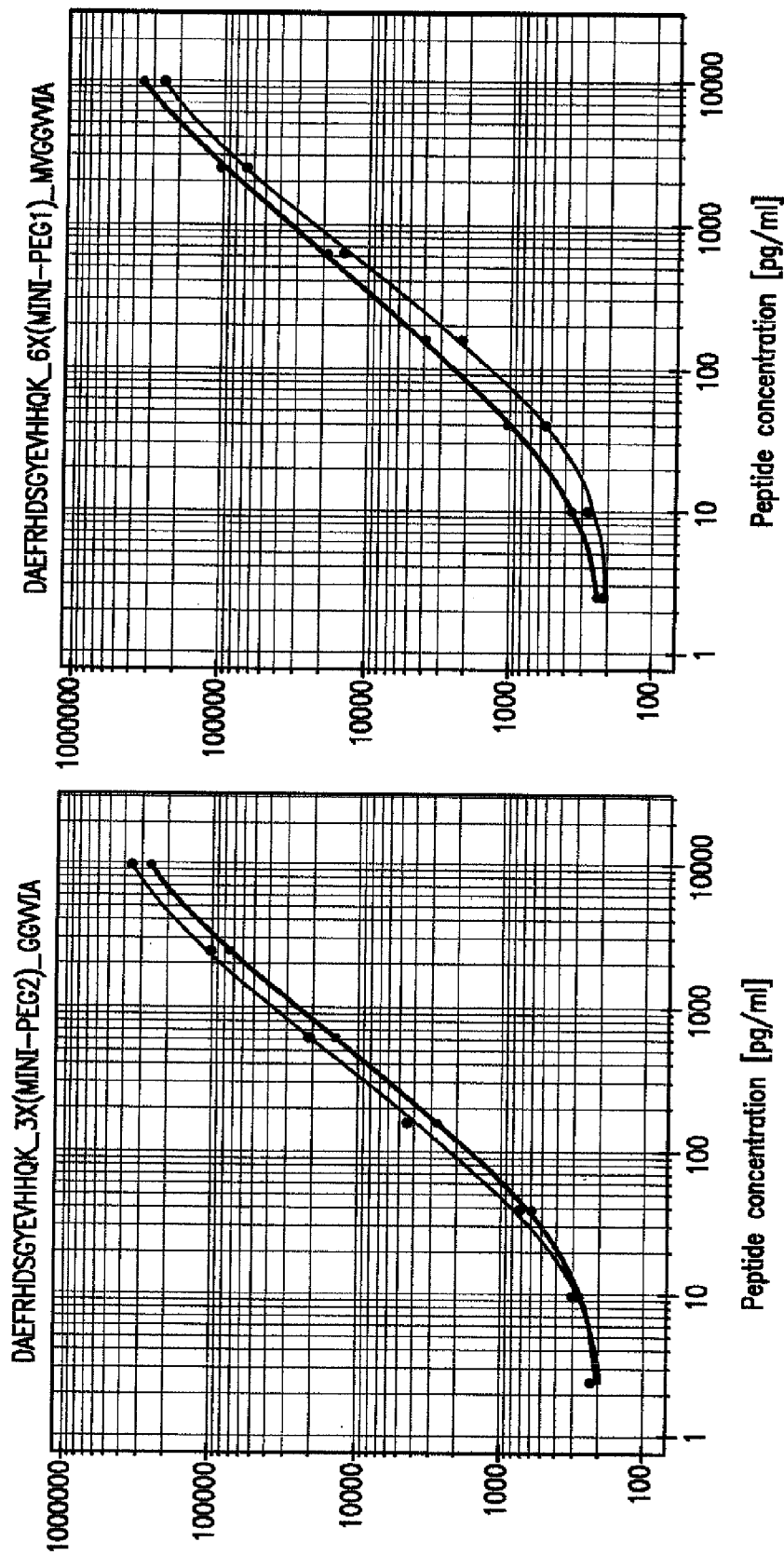
Figure 3C:
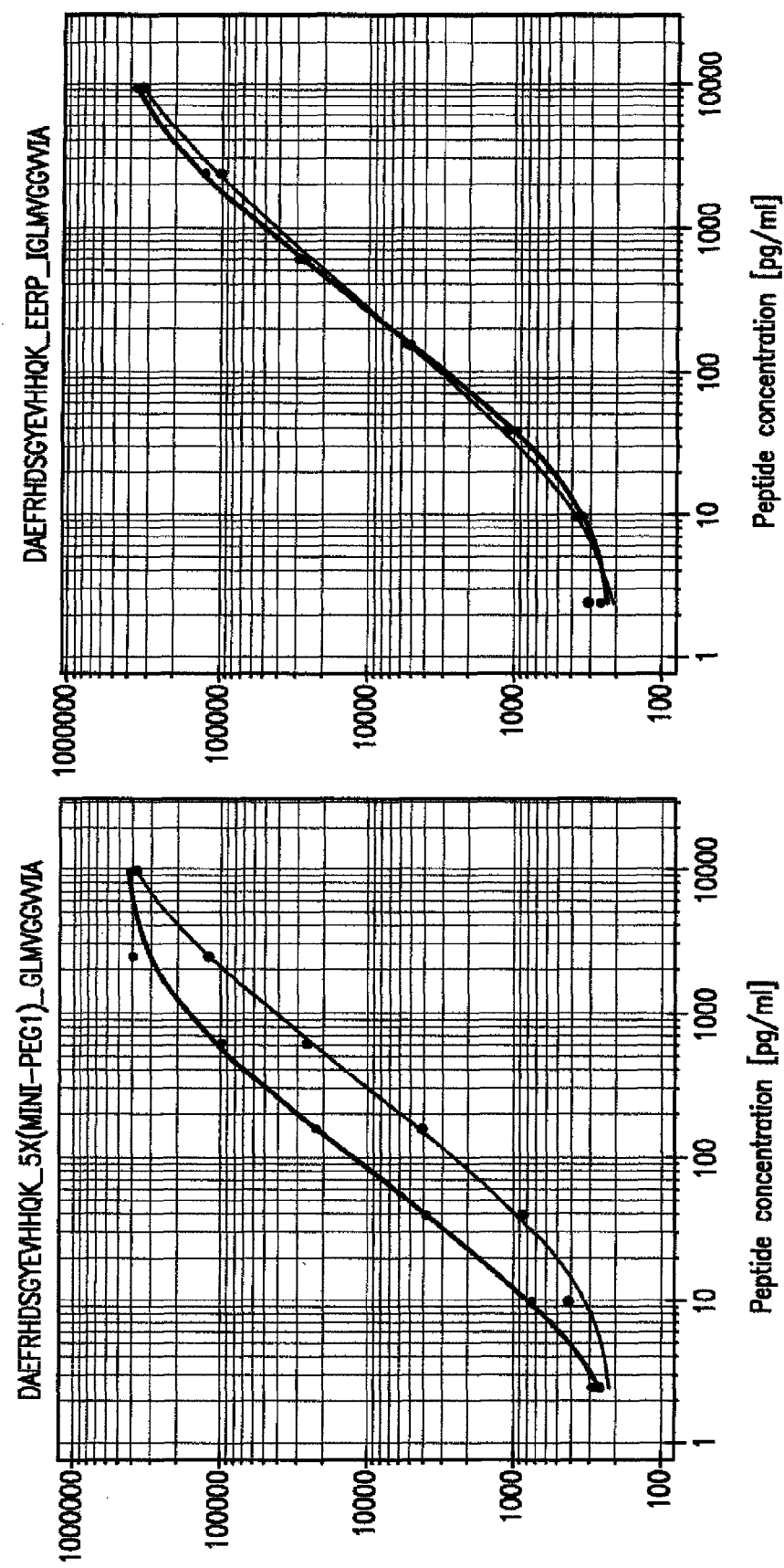

An example of a sandwich assay that can be used to measure $A\beta_{42}$ is shown in FIG. 2. Briefly, a biotin labeled anti-C-terminal $A\beta_{42}$ antibody (565) was immobilized to a 96 well Meso-Scale Discovery streptavidin coated plate (MesoScale Discovery Inc., Gaithersburg, Md. ((MSD)). Reference standard $A\beta_{42}$ peptides (full length with native sequence) were added to different wells. $A\beta_{42}$ peptides were captured by the immobilized capture antibody. A second ruthenium tagged (Ru) antibody to the N-terminus of $A\beta_{42}$ (26D6) was added, completing the sandwich. The complex was detected using an MSD sector 6000 instrument using ECL. The raw fluorescence units (RFU) measured by the instrument were fit to a 4-parameter logistic model to create a standard curve. In another example, several modified $A\beta_{42}$ peptides are used as a reference standard (Table 2, SEQ ID NOs:2, 4, 6, 12, 13, and 14). The standard curves generated by these modified calibrators are shown in FIGS. 3A-C.

TABLE 2

$A\beta_{42}$ Peptide and Modified Peptide Sequences and Descriptions

| Peptide/Modified Peptide Sequence | Description of Peptide/ Modified Peptide Sequence |
|---|---|
| DAEFRHDSGYEVHHQKLVFFAEDVGSNKGAIIGLMVGGVVIA (SEQ ID NO: 1) | native $A\beta_{42}$ sequence |
| DAEFRHDSGYEVHMVGGVVIA (SEQ ID NO: 2) | native $A\beta_{42}$ amino acids (1-14)(35-42 with no spacer in between |
| DAEFRHDSGYEVHHQKGGVVIA (SEQ ID NO: 3) | native $A\beta_{42}$ amino acids (1-16)(7-42) with no spacer in between |
| DAEFRHDSGYEVHHQKIGLMVGGVVIA (SEQ ID NO: 4) | native $A\beta_{42}$ amino acids (1-16)(32-42) with no spacer in between |
| DAEFRHDSGYEVHHQK<u>EERP</u>GGVVIA (SEQ ID NO: 5) | native $A\beta_{42}$ amino acids (1-16)-EERP-native $A\beta_{42}$ amino acids (37-42) |
| DAEFRHDSGYEVHHQK<u>EERP</u>IGLMVGGVVIA (SEQ ID NO: 6) | native $A\beta_{42}$ amino acids (1-16)-EERP-native $A\beta_{42}$ amino acids (32-42) |
| DAEFRHDSGYEVHHQK<u>DREERP</u>GGVVIA (SEQ ID NO: 7) | native $A\beta_{42}$ amino acids (1-16)-DREERP hydrophilic linker-native $A\beta_{42}$ amino acids (37-42) |
| DAEFRHDSGYEVHHQK<u>DREPNR</u>IGLMVGGVVIA (SEQ ID NO: 8) | native $A\beta_{42}$ amino acids (1-16)-DREPNR hydrophilic linker-native $A\beta_{42}$ amino acids (32-42) |
| (1-16)-<u>(Lys)m</u>-(37-42) (SEQ ID NO: 9) | native $A\beta_{42}$ amino acids (1-16)-up to 20 Lysine residues-native $A\beta_{42}$ amino acids (37-42) |

TABLE 2-continued

Aβ42 Peptide and Modified Peptide Sequences and Descriptions

| Peptide/Modified Peptide Sequence | Description of Peptide/ Modified Peptide Sequence |
|---|---|
| (1-16)-(Glu)n-(37-42) (SEQ ID NO: 10) | native Aβ42 amino acids (1-16)-up to 20 Glutamic acid residues-native Aβ42 amino acids (37-42) |
| (1-16)(Ala)p-(37-42) (SEQ ID NO: 11) | native Aβ42 amino acids (1-16)-up to 20 Alanine residues-native Aβ42 amino acids (37-42) |
| DAEFRHDSGYEVHHQK-PEG(20-ATOMS)3-GGVVIA (SEQ ID NO: 12) | native Aβ42 amino acids (1-16)-(PEG_20)3 linker-native Aβ42 amino acids (37-42) |
| DAEFRHDSGYEVHHQK-PEG(9-ATOMS)6-MVGGVVIA (SEQ ID NO: 13) | native Aβ42 amino acids (1-16)-(PEG_9)6 linker-native Aβ42 amino acids (35-42) |
| DAEFRHDSGYEVHHQK-PEG(9-ATOMS)5-IGLMVGGVIVIA (SEQ ID NO: 14) | native Aβ42 amino acids (1-16)-PEG_9)5 linker-native Aβ42 amino acids (32-42) |
| (X-Y)-Linker-(Z-42) | Generic: X,Y,Z, Linker to be specified |
| DAEFRHDSGYEVHHQKLVFFAEDVGSNKGAIIGLMVGGVV (SEQ ID NO: 15) | Aβ40 native sequence |

Example 2

Sandwich Aβ42 Assay Measuring Aβ42 In Biological Samples

An example of a sandwich Aβ42 assay measuring Aβ42 in biological samples is shown in Table 3. Biotin labeled anti-C-terminal Aβ42 antibody (565) was immobilized to a 96 well MSD streptavidin coated plate. Reference standard Aβ42 peptides (full length with native sequence) or a modified Aβ42 reference standard (SEQ ID NO:2) were added to different wells. Human CSF samples at different dilutions were placed in different wells. The plate was incubated 2 hours at room temperature to allow Aβ42 peptides to be captured by the immobilized capture antibody. A second ruthenium tagged (Ru) antibody to the N-terminus of Aβ42 (26D6) was added, completing the sandwich. The complex was detected using an MSD sector 6000 instrument using ECL. The raw fluorescence units (RFU) measured by the instrument were fit to a 4-parameter logistic model to create a standard curve. The measured concentrations of Aβ42 in human CSF samples are shown in Table 3.

TABLE 4

Measured Concentration of Aβ42 Peptide in Three Human Cerebrospinal (CSF) Samples

| | | Aβ42 Concentration (pg/ml) | |
|---|---|---|---|
| CSF sample | CSF dilution | Full length Aβ 1-42 Peptide | Modified Aβ xx-42 peptide |
| CSF-1 | 1:2 dil | Below limit of detection | Below limit of detection |
| CSF-1 | 1:4 dil | Below limit of detection | Below limit of detection |
| CSF-2 | 1:2 dil | 26.2 | 27.8 |
| CSF-2 | 1:4 dil | 54.0 | 56.8 |
| CSF-3 | 1:2 dil | 88.4 | 80.4 |
| CSF-3 | 1:4 dil | 134.4 | 126.4 |

Example 3

Aβ Peptide Based TNTRA-Assay Luminex Assay

Figure 4:
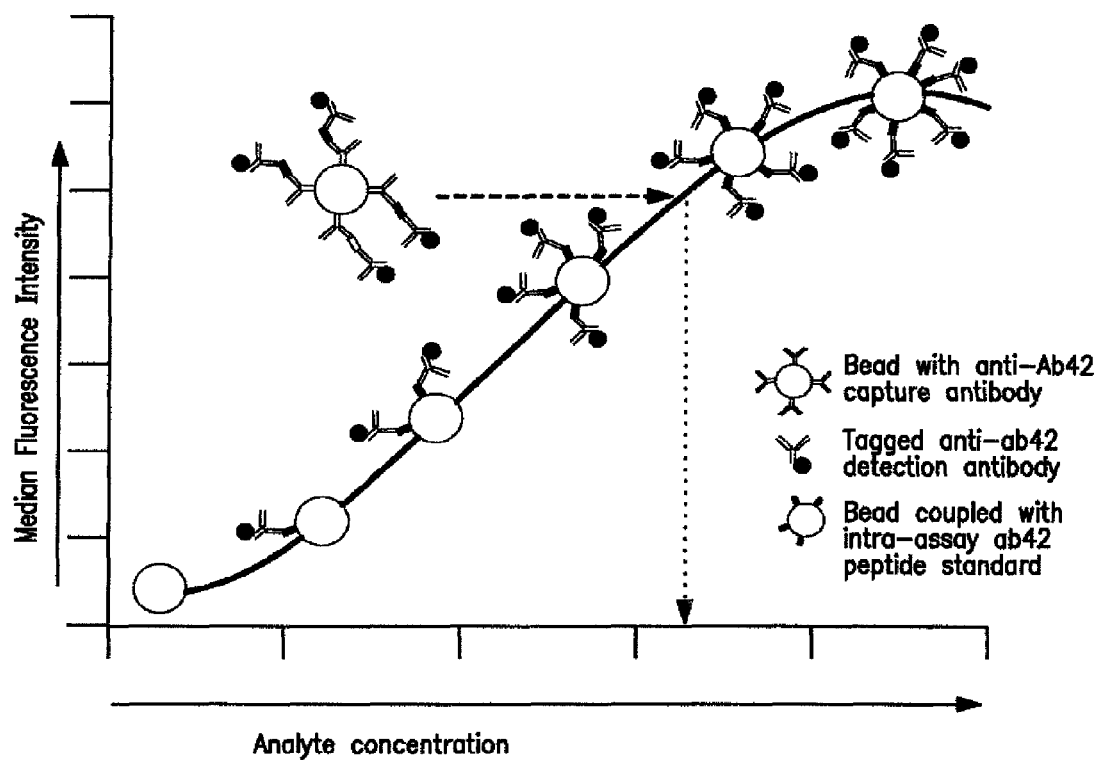
FIG. 4 shows a schematic of the $A\beta_{42}$ intra-assay bead approach.

FIG. 4 shows a schematic of the Aβ42 intra-assay bead approach. Bead sets coupled with different concentrations of Aβ42 standard peptides (or other native or modified A13 peptides) are combined with a bead set coupled with an anti-Aβ42-C-terminal specific capture antibody to form a suspension array. The array is incubated with a biological sample, where the Aβ42 peptide in the biological sample is captured by the bead coupled with anti-Aβ42 capture antibody. A tagged detection antibody specific to the N-terminus of the Aβ42 peptide is added to the suspension array, thereby binding to the captured Aβ42 peptide and also to the beads that have Aβ42 peptides coupled to their surface. The MFI values obtained from the beads with Aβ42 peptides coupled to their surface is used to generate an intra-assay calibration curve. The amount of Aβ42 in the biological sample is determined from the amount of captured Aβ42 on the bead coupled with the anti-Aβ42 capture using the intra-assay standard curve.

Antibodies and Reference Standards

The native full length Aβ42 and full length Aβ40 peptides (SEQ ID NOs: 1 and 15, respectively) were obtained from American Peptide Company. The 1 16B565.1 mouse anti-human Aβ42 C-terminus antibody and the 26D6-B2-B3 mouse anti-human Aβ42 N-terminus antibody were obtained via protein-G purification of culture supernatants produced by the relevant BMS owned hybridoma cell lines.

Phycoerythrin-streptavidin conjugate was obtained from Jackson Immunoresearch (West Grove, Pa.). Tween-20, 1-ethyl-3-[3 dimethylaminopropyl]carbodiimide hydrochloride (EDC), sodium azide, IgG free Bovine Serum Albumin (BSA), and sodium phosphate were purchased from Sigma-Aldrich Corporation (St. Louis, Mo.). Phosphate buffered saline (PBS) was obtained from Mediatech Incorporated (Herndon, Va.). Carboxylated Luminex beads were purchased from Bio-Rad Incorporated (Hercules, Calif.). Phycoerythrin label goat anti-mouse IgG antibody was obtained from Jackson Immunoresearch (West Grove, Pa.).

Covalent Coupling of Anti-A$\beta_{42}$ Capture Antibody to Luminex Beads

The 1 16B565.1 mouse anti-human A1342 C-terminus antibody was covalently coupled to the surface of carboxylated beads using a two-step carbodimide procedure. The beads were washed by centrifuging 1.25×10$^7$ beads for 5 min at 14000×g 4° C. in an Eppendorf 5415D centrifuge (Westbury, N.Y.). The supernatant was carefully removed and another 1.25×10$^7$ beads were dispensed and centrifuge for 5 min at 14000×g 4° C. The supernatant was again carefully removed and resuspended in 800 µl of 0.1M sodium phosphate buffer pH 4.8 (activation buffer). The beads were then vortexed for 15 seconds and sonicated for 15 seconds using a SPER SCIENTIFIC® LTD Ultrasonic Cleaner (Scottsdale, Ariz.). The beads were washed 2 additional times with activation buffer, and resuspended in 200 µl of freshly prepared 5 mg/ml EDC prepared in activation buffer. The beads were incubated in a rotator for 20 min RT protected from light. At the end of the EDC step, the beads were washed and resuspended in 1000 µl of 250 µg/ml capture antibody prepared in PBS and incubated for 1 hrs RT in a rotator protected from light. The beads were washed and incubated with 1 ml of blocking buffer (PBS, 1% (w/v) BSA, 0.02% (w/v) Tween-20) in a rotator for 1 hr RT protected from light. Finally, the beads were counted with a hemacytometer, resuspended in blocking buffer at 2×106 beads/ml, and stored protected from light at 4° C. until ready for use.

Surface Testing of Covalent Coupling Efficiency of A$\beta_{42}$ Capture Antibodies to Luminex Beads The presence of capture antibody on the bead surface was confirmed using surface testing. 50 µl of assay buffer (PBS, 1% (w/v) BSA, 0.05% (w/v) Tween 20, 0.05% (w/v) azide) containing 2500 beads were added to Millipore filter bottom plate wells (Bedford, Mass.). The beads were washed by placing the plate over a Millipore vacuum manifold (Bedford, Mass.) to remove the liquid and then resuspended in 100 µl/well of PBST wash buffer. Finally, the wash buffer was removed from the wells via vacuum and the beads were incubated with 100 µl/well of PE-Goat anti-mouse IgG diluted 1/100 in assay buffer. The plate was incubated on a 96-well plate shaker (Lab Line Instruments, Melrose Park, Ill.) at 300 rpm for 30 min RT protected from light. The beads were subsequently washed 3 times via vacuum filtration using 100 µl/well of wash buffer and resuspended in 100 µl/well of assay buffer. The MFI of at least 50 beads/well was measured using a Luminex$^{100}$ instrument obtained from Bio-Rad Laboratories (Hercules, Calif.) running Bioplex manager 4.1.1 software. An MFI of at least 20,000 was used to confirm the presence of usable quantities of antibody on the bead surface.

Covalent Coupling of Intra-Assay A$\beta_{40}$ Peptides to Luminex Beads

A$\beta_{40}$ native full length peptides (SEQ ID NO: 15) were prepared by reconstituting the lyophilized peptide in 2.5 ml PBS to give a final concentration of 10 mg/ml. A$\beta_{40}$ peptides were selected for this assay in lieu of A$\beta_{42}$ peptides because they still expressed the N-terminal A$\beta_{42}$ epitopes needed for the binding of 26D6 antibodies and the A$\beta_{40}$ peptides were more stable in aqueous buffers needed for conjugation. A$\beta_{40}$ peptides were diluted to different concentrations (shown in FIG. 5A) using diluent buffer (PBS, 1% (w/v) BSA, 0.02% (w/v) Tween-20). Each preparation of A$\beta_{40}$ peptide was covalently coupled to the surface of a selected bead set (different bead set for each concentration) using a two-step carbodimide procedure. Each bead set was washed by centrifuging 1.25×10$^7$ beads for 5 min at 14000×g 4° C. in an Eppendorf 5415D centrifuge (Westbury, N.Y.). The supernatant was carefully removed and 800 µl of 0.1 M sodium phosphate buffer pH 4.8 (activation buffer) was added. The beads were then vortexed for 15 seconds and sonicated for 15 seconds using a SPER SCIENTIFIC® LTD Ultrasonic Cleaner (Scottsdale, Ariz.). The beads were washed an additional time with activation buffer, and resuspended in 200 µl of freshly prepared 5 mg/ml EDC prepared in activation buffer. The beads were incubated in a rotator for 20 min RT protected from light. At the end of the EDC step, each bead set was washed and resuspended with the predetermined concentrations of A$\beta_{40}$ peptides and incubated for 1 hr RT in a rotator protected from light. The bead sets were washed and incubated with 1 ml of blocking buffer (PBS, 1% (w/v) BSA, 0.02% (w/v) Tween-20) in a rotator for 1 hr RT protected from light. Finally, the concentration of each bead set preparation was assessed by counting the beads with a hemacytometer. Each bead set was then resuspended in blocking buffer at 2×10$^6$ beads/ml, and stored protected from light at 4° C. until ready for use.

Testing of A$\beta_{40}$ Peptide Coupled Luminex Beads

The presence of A$\beta_{40}$ peptides which contain the N-terminal epitopes for the A$\beta_{42}$ N-terminal specific antibodies on the bead surface was confirmed using surface testing. 50 µl of assay buffer (PBS, 1% (w/v) BSA, 0.05% (w/v) Tween 20, 0.05% (w/v) azide) containing 2500 beads were added to Millipore filter bottom plate wells (Bedford, Mass.). The beads were washed by placing the plate over a Millipore vacuum manifold (Bedford, Mass.) to remove the liquid and the beads were resuspended in 100 µl/well of PBST wash buffer. Finally, the wash buffer was removed from the wells via vacuum and the beads were incubated with 100 µl/well of biotin labeled 26D6-B2-B3 antibody diluted in assay buffer. The plate was incubated on a 96-well plate shaker (Lab Line Instruments, Melrose Park, Ill.) at 300 rpm for 30 min RT protected from light. Following the incubation step, the beads were washed 4 times, resuspended in 50 µl/well of 1 µg/ml of Phycoerthrin-streptavidin conjugate, and incubated on a plate shaker for 20 min at RT protected from light. The beads were subsequently washed 3 times via vacuum filtration using 100 µl/well of wash buffer and resuspended in 100 µl/well of assay buffer. The MFI of at least 50 beads/well was measured using a Luminex100 instrument obtained from Bio-Rad Laboratories (Hercules, Calif.) running Bioplex manager 4.1.1 software. The MFI measured on each of the bead sets is shown in FIG. 5 A.

A$\beta_{42}$ Intra-Assay Analysis of Biological Samples

Figure 5B:
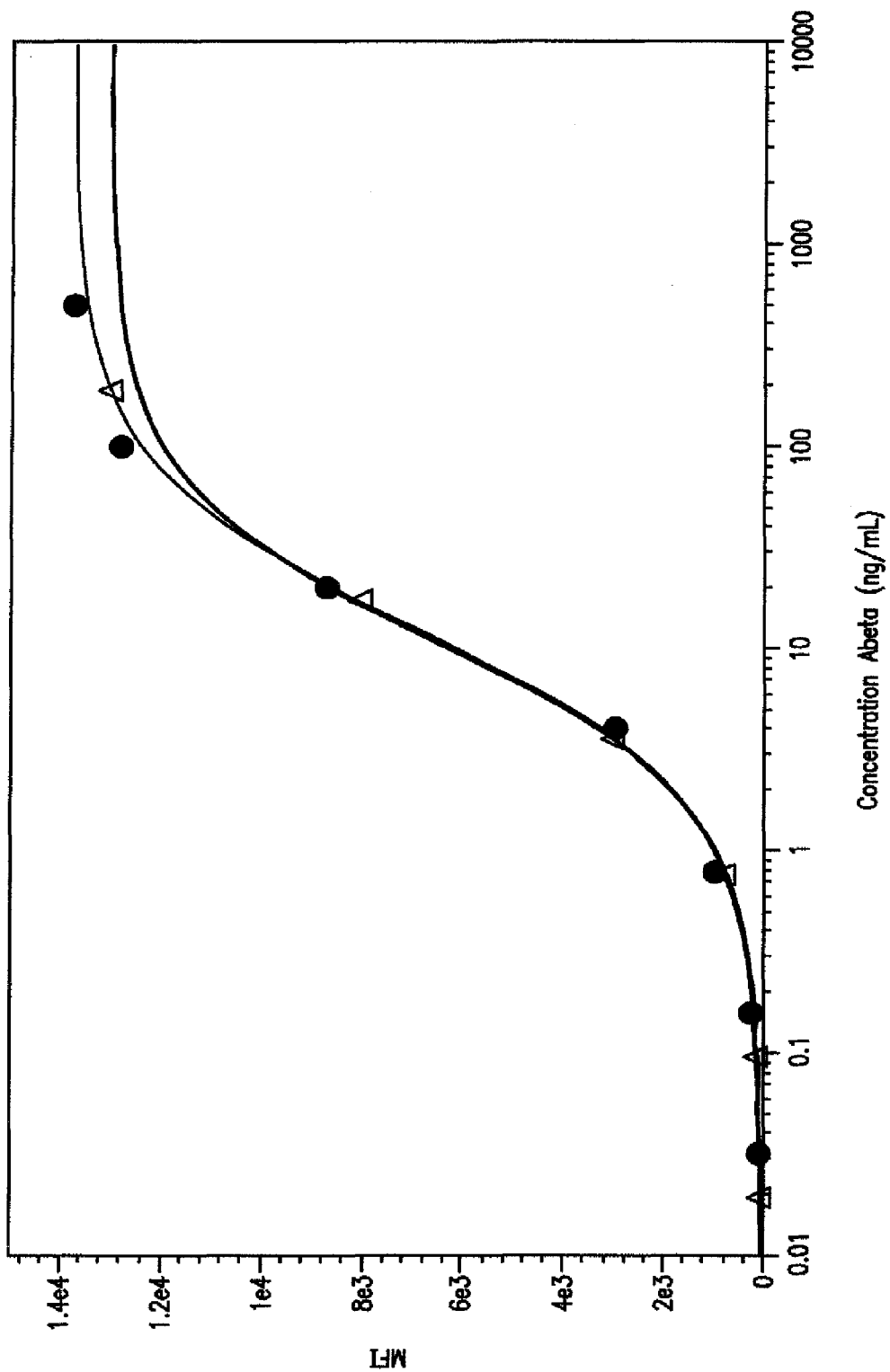
FIG. 5B shows 4-PL generated calibration curves from either the Aβ$_{40}$ intra-assay standards (circles) or from native Aβ$_{42}$ peptides as a soluble standard (triangles), similar to the curve shown in FIG. 2.

Samples analysis using the intra-assay Luminex based assay was performed by first mixing bead sets that were coupled with anti-C-terminal specific A$\beta_{42}$ 565 capture antibodies and bead sets that were coupled with different concentrations of A$\beta_{40}$ peptides (shown in FIG. 5A). 50 µl/well of the combined mixture of all bead sets at 50,000 beads/ml suspension prepared in assay buffer was added to each well of a pre-wet filter bottom 96-well plate. The beads were washed with 100 µl/well of assay buffer via vacuum filtration. The capture beads were resuspended in 50 µl of diluted human CSF samples, quality control samples (QC), different concentrations of full length native A$\beta_{42}$ peptides as reference standards, or different concentrations of modified A$\beta_{42}$ peptide standards in duplicate wells and incubated on a plate shaker for 1 hr at RT protected from light. 1.0 µg/ml anti-A$\beta_{42}$ 26 D6 reporter antibody labeled with biotin was added and then incubated on a plate shaker for 0.5 hrs at RT protected from light. Following the incubation step, the beads were washed 4 times, resuspended in 50 µl/well of 1 µg/ml of Phycoerthrin-streptavidin conjugate, and incubated on a plate shaker for 20 min at RT protected from light. Finally, the beads were washed 4 times and resuspended in 100 µl/well of assay buffer. The MFI of at least 50 beads per well was measured using a Bioplex Luminex instrument running Bioplex manager 5.1 software (Bio-Rad Laboratories, Hercules, Calif.). Standard curves were generated from the soluble $A\beta_{42}$ peptides or from the signals generated from the bead sets coated with different concentrations of $A\beta_{40}$ peptides (intra-standard) using a weighted 4-parameter logistic curve fit (FIG. 5B). The concentration of $A\beta_{42}$ peptides in the CSF or QC samples were calculated from the relevant standard curve, and are shown in FIG. 5C.

Example 4

Peptide Based Intra-Assay for IGFR1 with Luminex Beads

Below is another example of a peptide intra-assay based assay for the detection of phosphorylated tyrosine residues, 1 162 and 1 163, on human IGF-R1 receptors. Phosphorylated regions of Tau may also be used in the same manner.

Antibodies and Reference Standards

A custom made IGF1R [$\rho\gamma\rho\gamma^{1162/1163}$] peptide was provided by Cambridge Research Biochemicals Ltd (UK). Mouse anti-IGFIR capture antibody was obtained from Calbiochem (San Diego, Calif.) and the rabbit anti-phosphotyrosine (1162/1163)-IGF1R reporter antibody was purchased from Millipore (Billerica, Mass.). Phycoerythrin label goat anti-rabbit antibody was obtained from Jackson Immunoresearch (West Grove, Pa.). Tween-20, 1-ethyl-3-[3 dimethylaminopropyl]carbodiimide hydrochloride (EDC), sodium azide, IgG free Bovine Serum Albumin (BSA), and sodium phosphate were purchased from Sigma-Aldrich Corporation (St. Louis, Mo.). Phosphate buffered saline (PBS) was obtained from Mediatech Incorporated (Herndon, Va.). Carboxylated Luminex beads were purchased from Bio-Rad Incorporated (Hercules, Calif.). Normal healthy PBMC samples were obtained from In house donors (BMS, NJ). The PBMC samples were treated with either PBS or 1OO ng/ml of purified human IGF 1 (Genetex Inc, TX) for 10 min at 37° C. to induce phosphorylation of IGFR present on the cells. The cells were washed, lysed with a modified RIPA buffer, and stored at −80° C.

Covalent Coupling of Anti-IGF-R1 Capture Antibody to Luminex Beads

The mouse anti-human IGF 1R capture antibody was covalently coupled to the surface of carboxylated beads using a two-step carbodimide procedure. The beads were washed by centrifuging $1.25\times10^7$ beads for 5 min at 14000×g 4° C. in an Eppendorf 5415D centrifuge (Westbury, N.Y.). The supernatant was carefully removed and another $1.25\times10^7$ beads were dispensed and centrifuged for 5 min at 14000×g 4° C. The supernatant was again carefully removed and re-suspended in 800 µl of 0.1 M sodium phosphate buffer pH 4.8 (activation buffer). The beads were then vortexed for 15 seconds and sonicated for 15 seconds using a SPER SCIENTIFIC® LTD Ultrasonic Cleaner (Scottsdale, Ariz.). The beads were washed 2 additional times with activation buffer, and resuspended in 200 µl of freshly prepared 5 mg/ml EDC prepared in activation buffer. The beads were incubated in a rotator for 20 min RT protected from light. At the end of the EDC step, the beads were washed and resuspended in 1000 µl of 250 µg/ml capture antibody prepared in PBS and incubated for 1 hr RT in a rotator protected from light. The beads were washed and incubated with 1 ml of blocking buffer (PBS, 1% (w/v) BSA, 0.02% (w/v) Tween-20) in a rotator for 1 hr RT protected from light. Finally, the beads were counted with a hemacytometer, resuspended in blocking buffer at 2×106 beads/ml, and stored protected from light at 4° C. until ready for use.

Testing of Covalent Coupled IGF-R1 Capture Antibodies to Luminex Beads

The presence of capture antibody on the bead surface was confirmed using surface testing. 50 µl of assay buffer (PBS, 1% (w/v) BSA, 0.05% (w/v) Tween 20, 0.05% (w/v) azide) containing 2500 beads were added to Millipore filter bottom plate wells (Bedford, Mass.). The beads were washed by placing the plate over a Millipore vacuum manifold (Bedford, Mass.) to remove the liquid and the beads were resuspended in 100 µl/well of PBST wash buffer. Finally, the wash buffer was removed from the wells via vacuum and the beads were incubated with 100 µl/well of PE-GAM diluted 1/100 in assay buffer. The plate was incubated on a 96-well plate shaker (Lab Line Instruments, Melrose Park, Ill.) at 300 rpm for 30 min RT protected from light. The beads were subsequently washed 3 times via vacuum filtration using 100 µl/well of wash buffer and resuspended in 100 µl/well of assay buffer. The MFI of at least 50 beads/well was measured using a Luminex[100] instrument obtained from Bio-Rad Laboratories (Hercules, Calif.) running Bioplex manager 4.1.1 software. An MFI of at least 20,000 was used to confirm the presence of usable quantities of antibody on the bead surface.

Covalent Coupling of Intra-Assay IGF-R1 Peptide Standards to Luminex Beads

IGF 1 R [P YPY 1162/1163] reference standard peptides were prepared by reconstituting the lyophilized peptide in 2.5 ml PBS to give a final concentration of 1O mg/ml. Initial 10 fold dilution with subsequent 10-fold were made using diluent buffer (PBS, 1% (w/v) BSA, 0.02% (w/v) Tween-20). The phospho-IGFIR peptide was covalently coupled to the surface of four different sets of carboxylated beads at four different concentrations using a two-step carbodimide procedure. The bead sets were washed by centrifuging $1.25\times10^7$ beads for 5 min at 14000×g 4° C. in an Eppendorf 5415D centrifuge (Westbury, N.Y.). The supernatant was carefully removed and 800 µl of 0.1M sodium phosphate buffer pH 4.8 (activation buffer) was added. The beads were then vortexed for 15 seconds and sonicated for 15 seconds using a SPER SCIENTIFIC® LTD Ultrasonic Cleaner (Scottsdale, Ariz.). The beads were washed an additional time with activation buffer, and resuspended 200 µl of freshly prepared 5 mg/ml EDC prepared in activation buffer. The beads were incubated in a rotator for 20 min RT protected from light. At the end of the EDC step, each beads were washed and resuspended with individual concentration of 1000, 100, 10 and 1 ng/ml of phospho-IGF IR peptide made from a 10-fold serial dilutions of 10 mg/ml prepared in PBS. The beads were then incubated for 1 hr RT in a rotator protected from light. The beads were washed and incubated with 1 ml of blocking buffer (PBS, 1% (w/v) BSA, 0.02% (w/v) Tween-20) in a rotator for 1 hr RT protected from light. Finally, the beads were counted with a hemacytometer, resuspended in blocking buffer at $2\times10^6$ beads/ml, and stored protected from light at 4° C. until ready for use.

Testing of IGF-R1 Peptide Coupled Luminex Beads

The presence of phospho-IGFIR peptide on the bead surface was confirmed using surface testing. 50 µl of assay buffer (PBS, 1% (w/v) BSA, 0.05% (w/v) Tween 20, 0.05% (w/v) azide) containing 2500 beads were added to Millipore filter bottom plate wells (Bedford, Mass.). The beads were washed by placing the plate over a Millipore vacuum manifold (Bedford, Mass.) to remove the liquid and the beads were resuspended in 100 μl/well of PBST wash buffer. Finally, the wash buffer was removed from the wells via vacuum and the beads were incubated with 100 μl/well of rabbit anti-phospho-IGF-R1 antibody diluted in assay buffer. The plate was incubated on a 96-well plate shaker (Lab Line Instruments, Melrose Park, Ill.) at 300 rpm for 30 min RT protected from light. Following the incubation step, the beads were washed 4 times, resuspended in 50 μl/well of ˆg/ml of phycoerthrin labeled goat anti-rabbit IgG conjugate, and incubated on a plate shaker for 20 min at RT protected from light. The beads were subsequently washed 3 times via vacuum filtration using 100 μl/well of wash buffer and resuspended in 100 μl/well of assay buffer. The MFI of at least 50 beads/well was measured using a Luminex[100] instrument obtained from Bio-Rad Laboratories (Hercules, Calif.) running Bioplex manager 4.1.1 software. phospho-IGF 1R peptide.

IGF-R1 Intra-Assay Analysis of Biological Samples

Figure 6A:
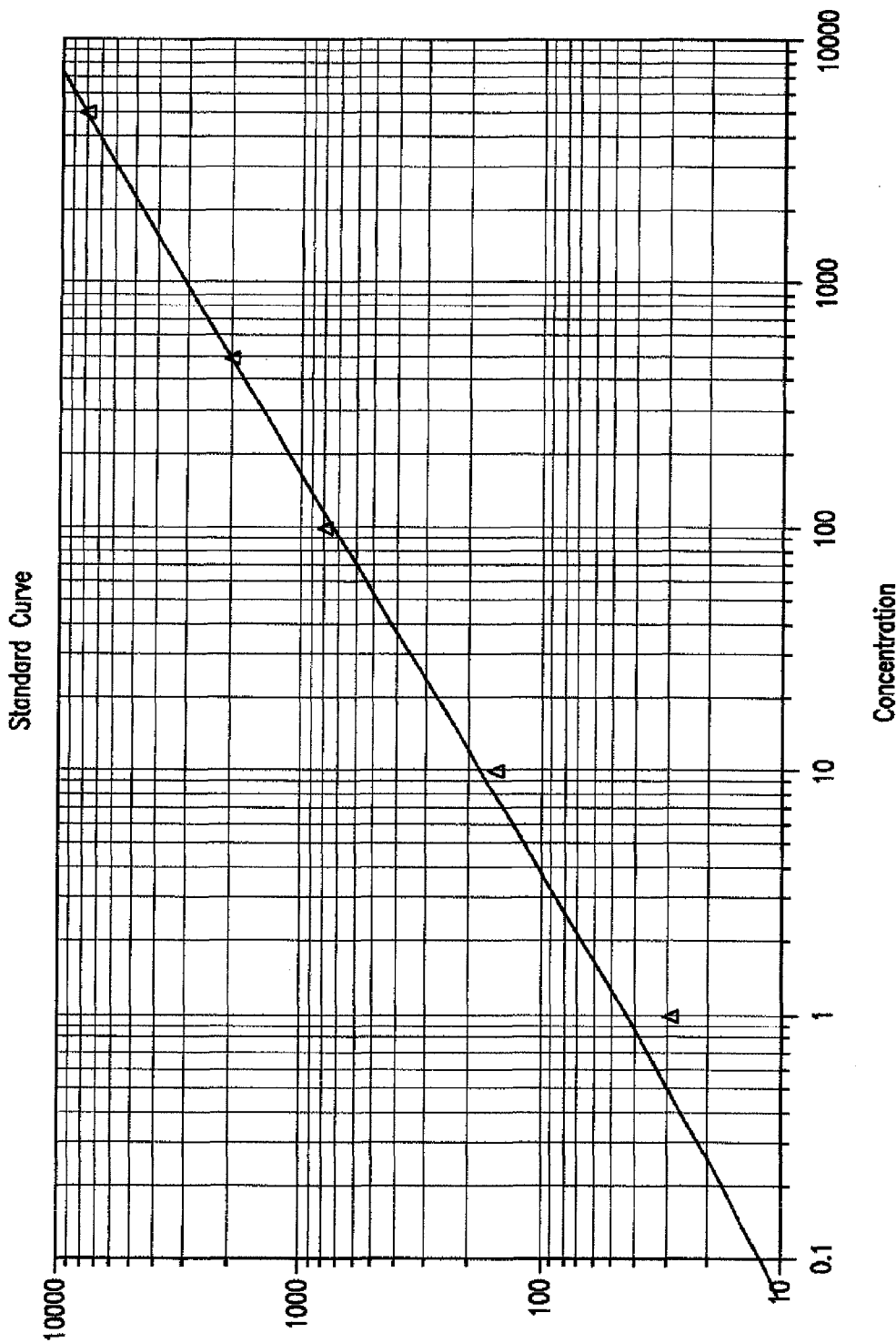
FIGS. 6A-B show the levels of phosphorylated insulin growth factor receptor 1 (IGF-R1) in human peripheral blood mononuclear cell lysates. A 4 parameter calibration curve was generated from the MFI values on the different bead sets (FIG. 6A) and used to determine the relative levels of phosphorylated IGF-R1 in PBMC lysates (FIG. 6B).
Figure 6B:
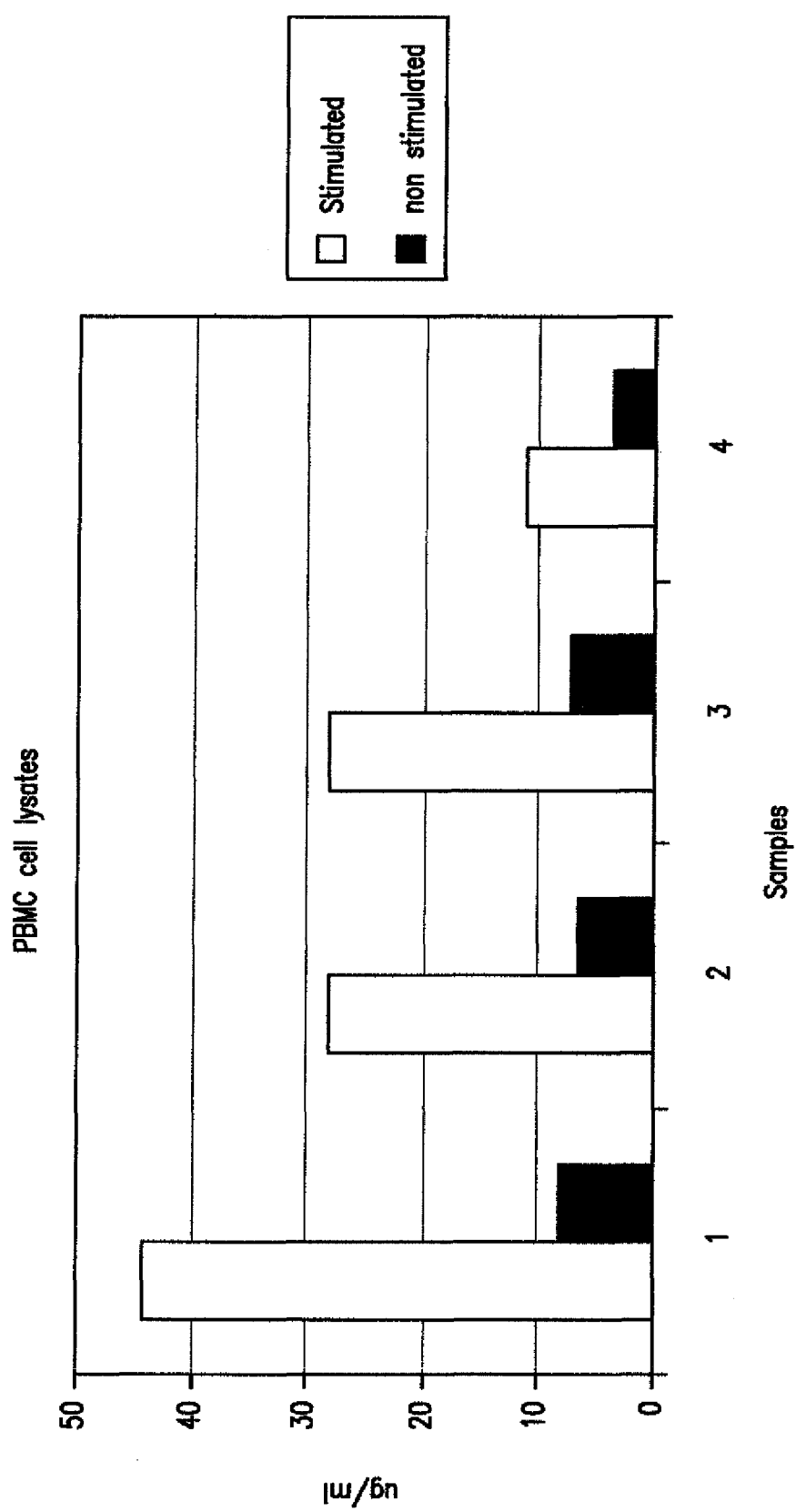

Sample analysis using the Luminex based assay was performed by adding 50 μl of a 50,000 beads/ml of capture antibody suspension prepared in assay buffer to each well of a pre-wet filter bottom 96-well plate. The beads were washed with 100 μl/well of assay buffer via vacuum filtration. The capture beads were resuspended in 50 μl of diluted samples, or quality control samples (QC) in duplicate wells and incubated on a plate shaker for 1 hr at RT protected from light. The beads were washed 4 times, resuspended in 50 μl of a 50,000 beads/ml of the four different bead sets of peptide mentioned in section 2.2.3. The beads were filtered, resuspended in 50 μl/well of 1.0 μg/ml anti-phospho IGF1R reporter antibody, and incubated on a plate shaker for 0.5 hrs at RT protected from light. Following the incubation step, the beads were washed 4 times, resuspended in 50 μl/well of ˆg/ml of PE-Goat anti rabbit IgG, and incubated on a plate shaker for 20 min at RT protected from light. Finally, the beads were washed 4 times and resuspended in 100 μl/well of assay buffer. The MFI of at least 50 beads per well was measured using a Bioplex Luminex instrument running Bioplex manager 4.1 software (Bio-Rad Laboratories, Hercules, Calif.). The standard curve generated from the phospho-IGF-R1 intra-standard curve is shown in FIG. 6A. The phospho-IGFIR concentration in each of the PBMC lysate samples using the intra-assay 4-parameter logistic curve fit is shown in FIG. 6B.

Example 5

Characterization of Aβ Peptides

Peptides

All peptides were received as lyophilized powder. Modified peptides were obtained from GenScript (GS) and Anaspec (AN). These peptides were synthesized using solid phase methods known to those skilled in the art (See, for example, Barany, G. et al, The Peptides: Analysis, Synthesis, Biology—Special Methods in Peptide Synthesis, Part A, Vol. 2, pp. 3-284, Gross, E. et al, eds., Academic Press, New York, publ. (1980); and in Stewart, J. M. et al, Solid-Phase Peptide Synthesis, 2nd Edition, Pierce Chemical Co., Rockford, Ill., publ. (1984)).

Figure 13:
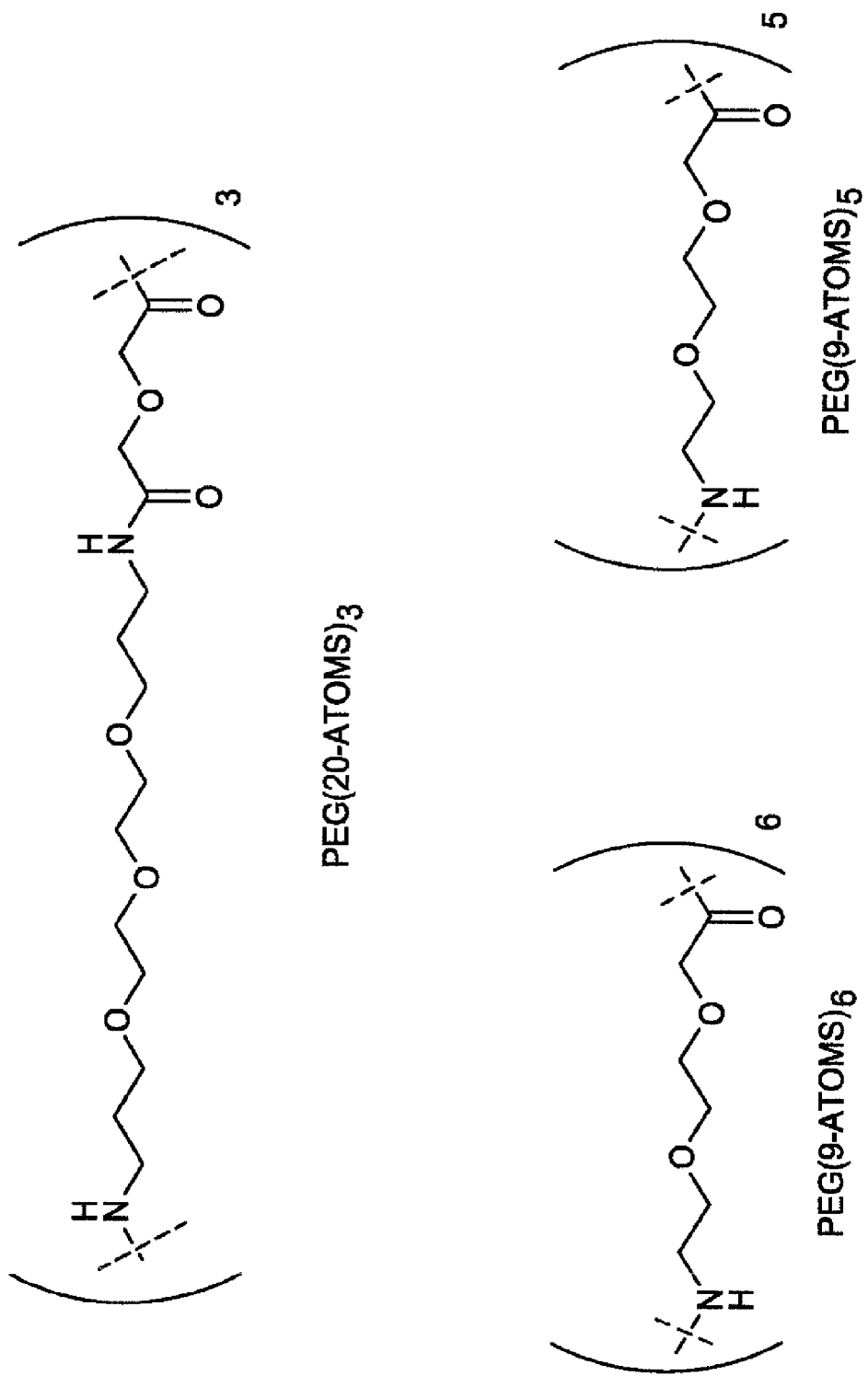
FIG. 13 shows the structures of the polyethylene glycol spacers incorporated into the modified Aβ$_{(1-42)}$ peptides.

GS 1-6 and AN7 peptides were received and reconstituted in ddH20 to a concentration of 1 mg/ml. These were then aliquoted out into 100 μl aliquots in the 1.4 ml blank tubes PP, round Matrix (Thermo Scientific, cat#4249, lot 1030509). The full length Aβ$_{42}$ peptide was purchase from MSD (lot # T03080X1). This peptide was diluted in DMSO to make a solution of 0.1 mg/ml. This was then aliquoted out in 100 μl aliquots in the 1.4 ml blank tubes. These peptides were kept frozen at −70° C. for storage. FIG. 13 shows the structures of the polyethylene glycol spacers incorporated into the modified Aβ$_{(1-42)}$ peptides.

TABLE 5

List of Aβ Peptides

| GS# | Peptide Sequence | % Purity (HPLC) | MW |
|---|---|---|---|
| GS 1 | DAEFRHDSGYEVHHQK-{PEG(20-atoms} 3-GGVVIA(SEQ ID NO: 12) | 95 | 3406.71 |
| GS 2 | DAEFRHDSGYEVHHQK-{PEG(9-atoms}6-MVGGVVIA (SEQ ID NO: 13) | 95 | 3553.02 |
| GS 3 | DAEFRHDSGYEVHHQK-PEG(9-ATOMS)5-IGLMVGGVVIA (SEQ ID NO: 14) | 95 | 3691.15 |
| GS 4 | DAEFRHDSGYEVHHQKEERPIGLMVGGVVIA (SEQ ID NO: 6) | 96 | 3476.91 |
| GS 5 | DAEFRHDSGYEVHHQKDREPNRIGLMVGGVV IA (SEQ ID NO: 8) | 97 | 3733.17 |
| GS 6 | DAEFRHDSGYEVHHQKIGLMVGGVVIA (SEQ ID NO: 4) | 98 | 2965.37 |
| AN 7 | DAEFRHDSGYEVHMVGGVVIA (SEQ ID NO: 2) | 90 | 2288.49 |
| FL | DAEFRHDSGYEVHHQKLVFFAEDVGSNKGA IIGLMVGGVVIADAEFRHDSGYEVHMVGGV VIA (SEQ ID NO: 19) | | |

Dynamic Light Scattering

The novel peptides (GenScript) were received as dry powders, and two sets of stock samples were prepared by weighing small amounts (~0.5 mg each) in 1.8 ml polypropylene tubes and dissolving in a simple phosphate buffer (10 mM Na$_2$HPO$_4$, pH 7.4, 10 mM NaCl, prepared in 99.9% D20; filtered through 0.2 μm filter). One set was prepared at 1.0 mg/ml, the second set was prepared at 0.10 mg/ml, and stored at room temperature. Peptides were dissolved by vortexing for 1 min, and centrifuged in a microcentrifuge for 5 min at 14,000 rpm, at room temperature. For Aβ$_{42}$ samples (MSD), vials containing 0.1 mg peptide were suspended in 1.0 ml buffer, and treated as above. A volume (200 μl) of each centrifuged 1.0 mg/ml stock was transferred to a 0.5 ml polypropylene tube, and provided for NMR analysis.

The absorbance spectra of all samples were recorded (220-750 nm) using a NANODROP® ND-1000 instrument, and blanked against the buffer. Dynamic light scattering analysis was conducted on the peptides in a 384 well polystyrene plate (CORNING®, type 3540) with a Wyatt DLS DynaPro plate reader. Data collection and analysis was completed using software from the manufacturer (DYNAMICS, versions 7.0.0.94 and 7.0.1.12). Each peptide was evaluated in triplicate with 30 μl loaded per well, and overlaid with 5 μl mineral oil, to minimize evaporation. Buffer blanks were also included in the analysis for comparison. After loading the plate, a transparent adhesive sealing tape cover was applied to the plate and the plate was centrifuged for 2 min at 1000 rpm. Each sample on the plate was read 30 times, 5 sec per acquisition, maintaining a temperature of 25° C. Data sets were collected on both the 1.0 mg/ml and 0.10 mg/ml samples over the course of 27 days. The adhesive cover was removed to read the samples in the plate reader, and used to cover the plate between readings over the 27 day time course.

Figure 7A:
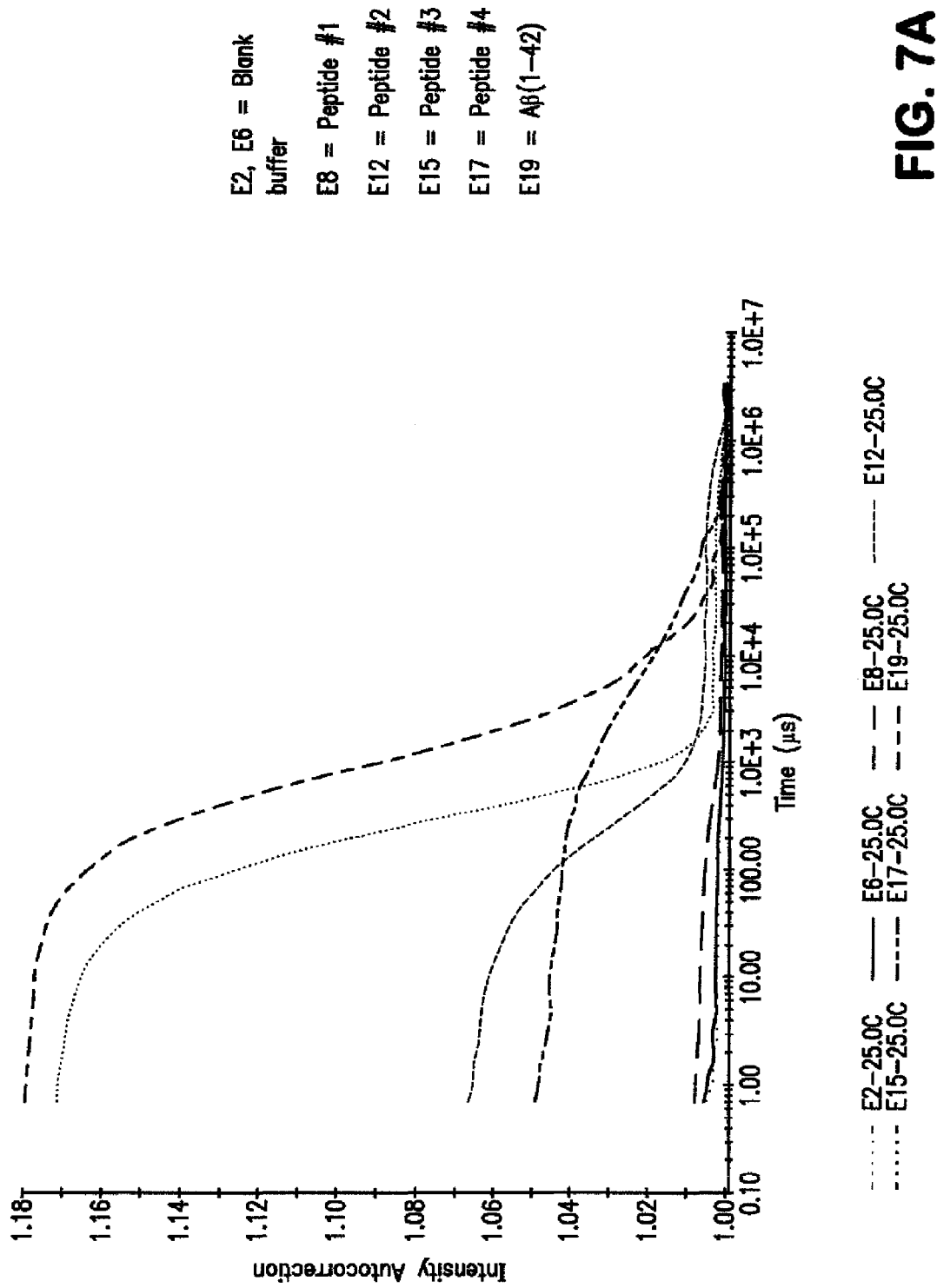
FIGS. 7A-F show DLS data.
Figure 7B:
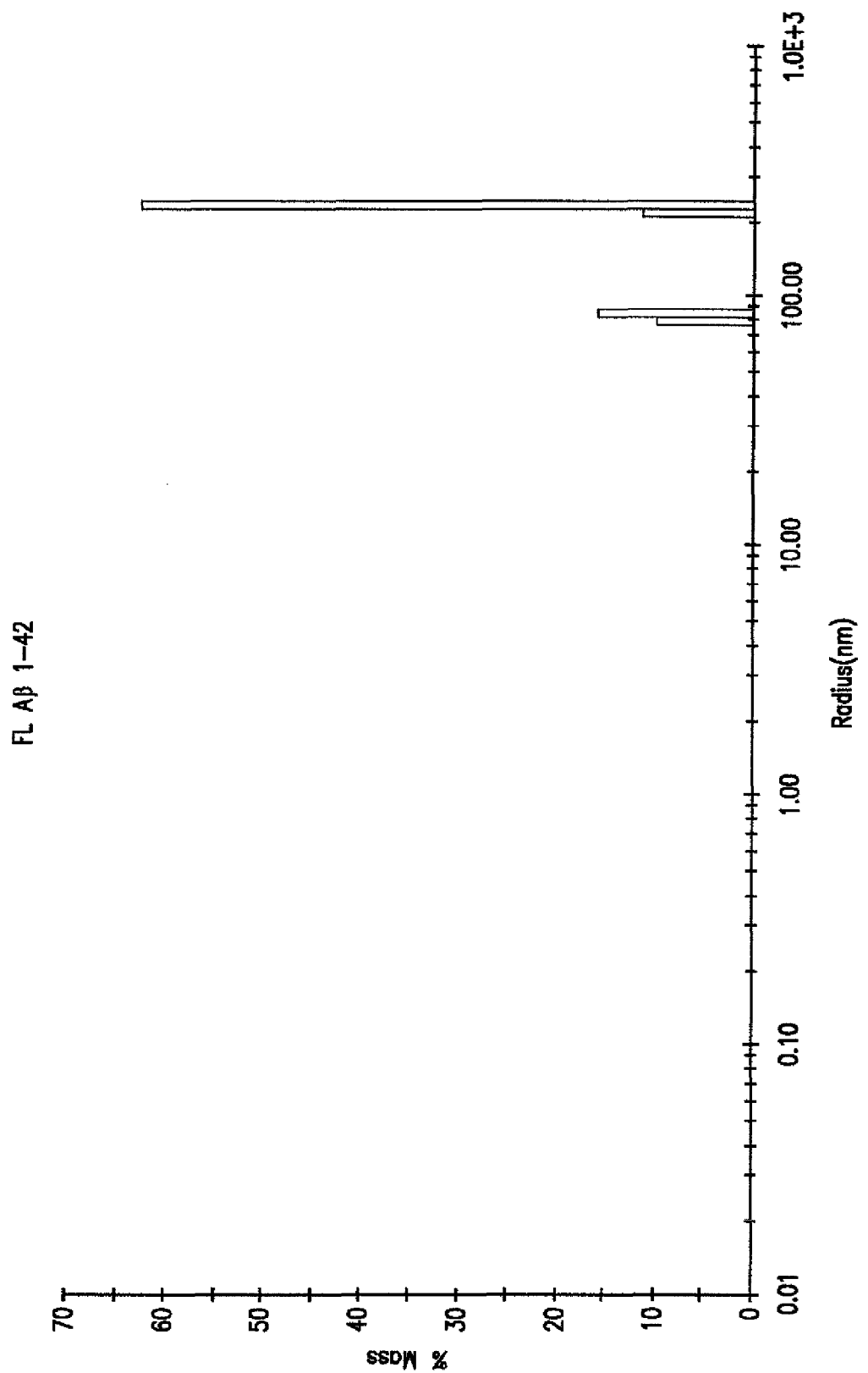
Figure 7C:
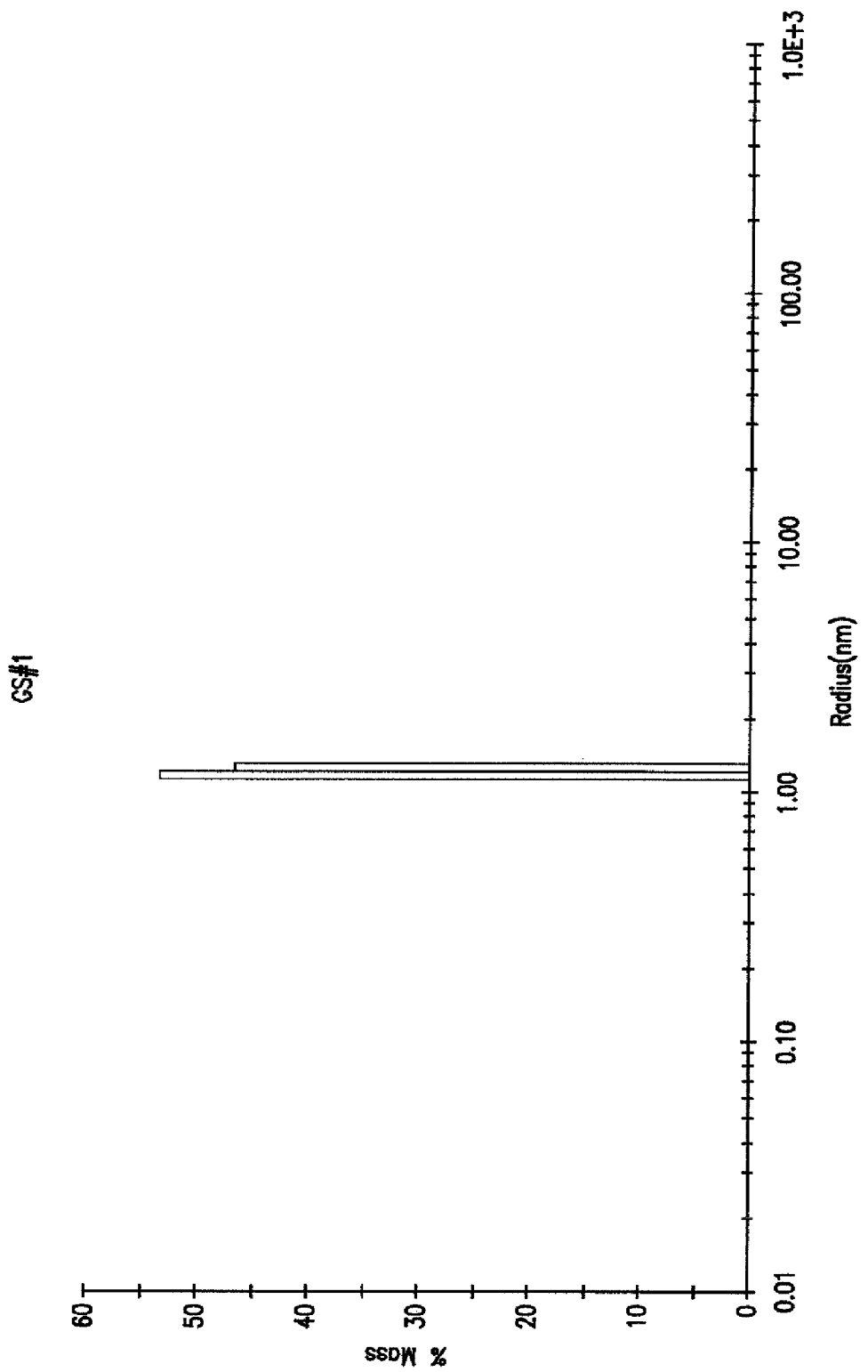
Figure 7D:
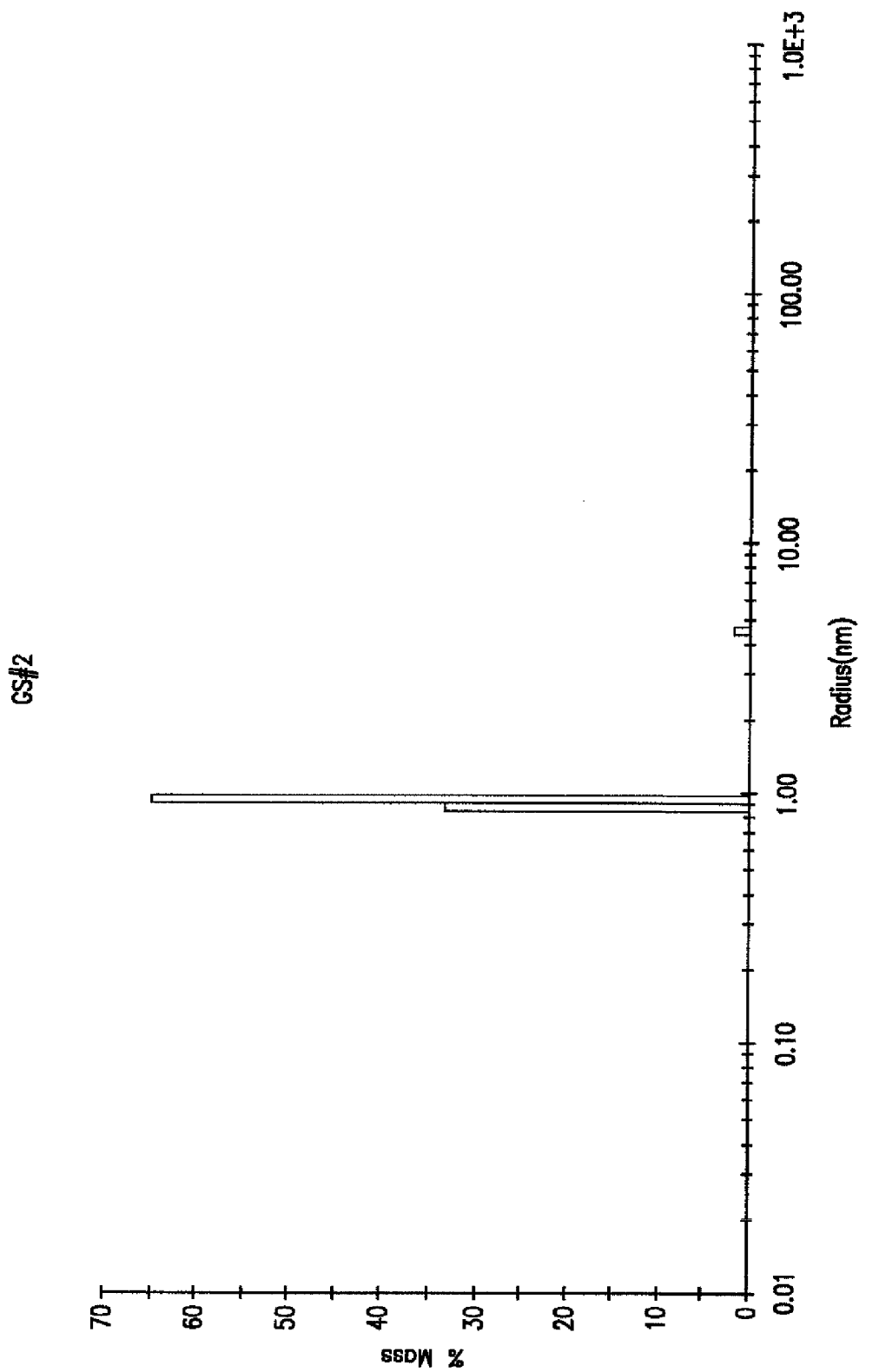
Figure 7E:
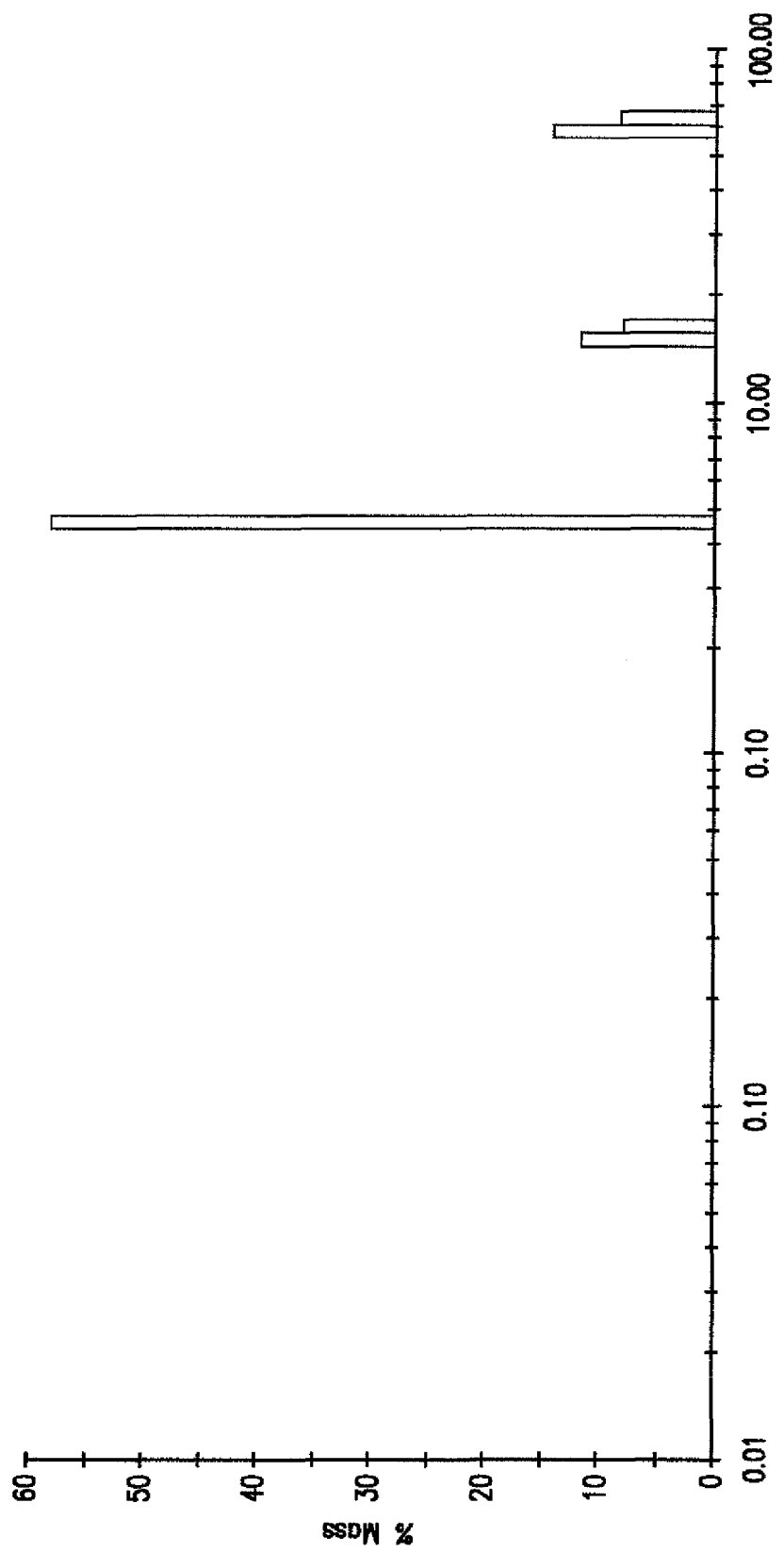
Figure 7F:
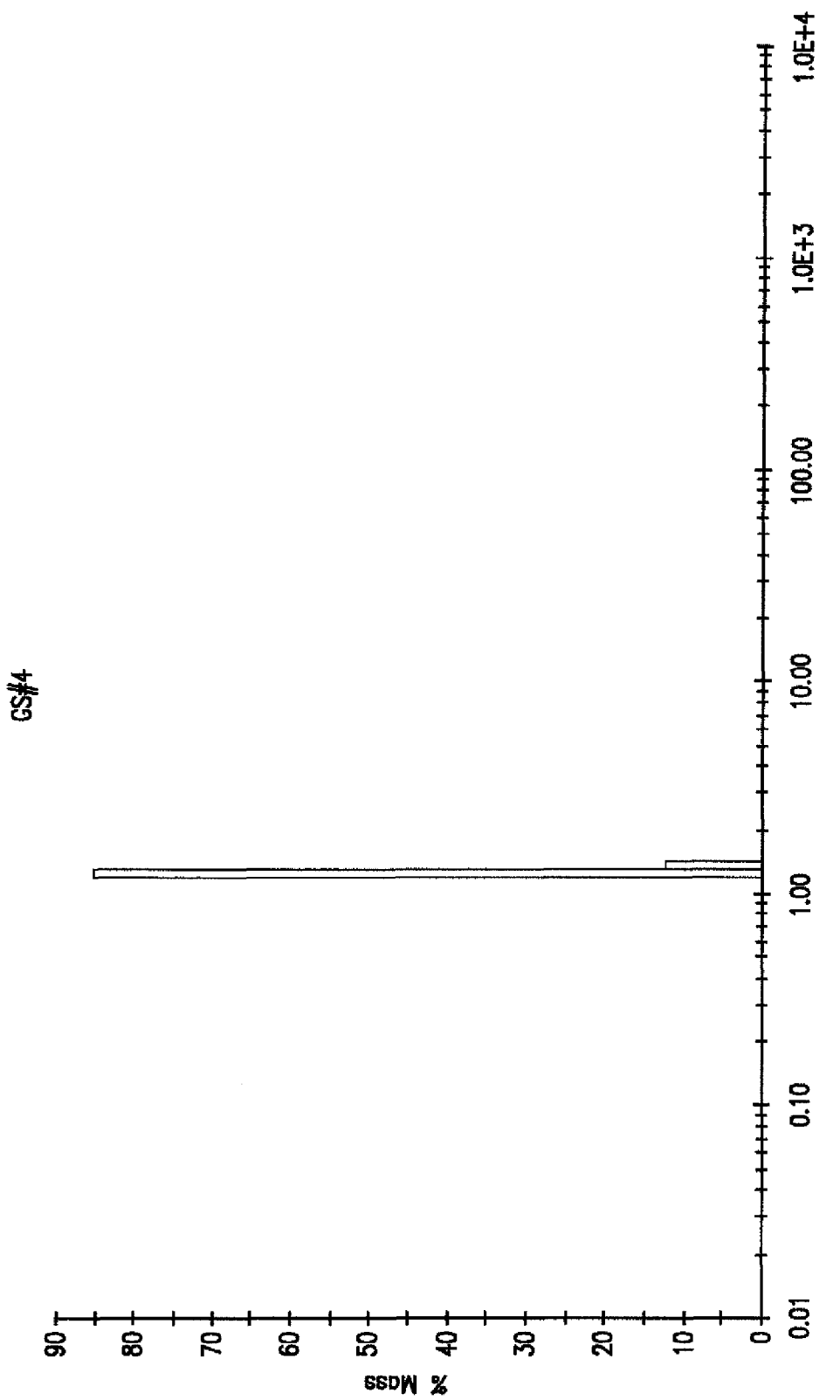

FIGS. 7A through 7F show dynamic light scattering data. In FIGS. 7A-F, the full length $A\beta_{42}$ peptide was subjected to DLS analysis and compared to four representative modified peptides. The full length peptide was shown to be aggregated with results that calculated the radius of the different aggregate species to be between 82 and 23 lnm in length. This adds up to large molecular weight aggregates in the solution. However, the modified peptides remain monomeric as determined by both molecular weights as well as radius. GS#3 was contrasted with the other peptides because it did retain some aggregation (FIG. 7E). These results demonstrate that the modified peptides which are lacking an aggregation domain, do in fact remain monomeric in solution. FIG. 7a represents the raw data accumulated for all five peptides. Shown is the intensity autocorrelation versus time. The higher the intensity autocorrelation number is represents larger diameters of the peptides in solution. FIGS. 7b-7f depict the percent mass versus the radius of the peptides. Monomeric peptides would be represented by a larger percent mass at the smaller radius size. The larger aggregated peptides have smaller percent masses at a higher radius size.

TABLE 6

Summary of DLS data

| Item | | Radius (nm) | % Pd | Mw-R (kDa) | % Intensity | % Mass |
|---|---|---|---|---|---|---|
| GS#1 | Peak 1 | 1.2 | 4.6 | 5.0 | 6.3 | 99.9 |
| | Peak 2 | 48.4 | 3.9 | 29512.0 | 93.7 | 0.1 |
| GS#2 | Peak 1 | 0.9 | 4.3 | 3.0 | 1.6 | 98.0 |
| | Peak 2 | 4.6 | 1.9 | 117.0 | 3.4 | 1.8 |
| | Peak 3 | 36.9 | 3.8 | 15580.0 | 76.1 | 0.1 |
| | Peak 4 | 172.0 | 4.5 | 572266.0 | 18.9 | 0.1 |
| GS#3 | Peak 1 | 4.5 | 0.0 | 119.0 | 0.4 | 57.9 |
| | Peak 2 | 15.7 | 4.5 | 2101.0 | 4.8 | 19.7 |
| | Peak 3 | 61.6 | 4.5 | 51794.0 | 94.8 | 22.4 |
| GS#4 | Peak 1 | 1.3 | 3.2 | 6.0 | 3.8 | 97.7 |
| | Peak 2 | 6.0 | 0.0 | 225.0 | 0.6 | 0.2 |
| | Peak 3 | 27.0 | 4.5 | 7527.0 | 5.2 | 0.0 |
| | Peak 4 | 127.0 | 4.3 | 283287.0 | 25.1 | 0.2 |
| FL Aβ1-42 | Peak 1 | 82.9 | 4.4 | 103812.0 | 50.4 | 26.1 |
| | Peak 2 | 231.0 | 3.2 | 1149570.0 | 49.6 | 73.9 |

Circular Dichroism

Circular dichroism (CD) spectra were collected using an Aviv Model 202 Circular dichroism spectrometer. Samples were pipetted in 1 mm path length quartz cuvettes, and scanned from 260-185 nm. Parameters for collecting data include spectral bandwidth of 1.00 nm, a step size of 1.0 nm, an averaging time of 20 sec per point, and temperature set at 25° C. Samples were stored in the quartz cuvettes at room temperature, and scanned over a time course of 23 days. Raw data was corrected for blank buffer contributions, and presented in the format of mdeg versus wavelength.

Figure 8:
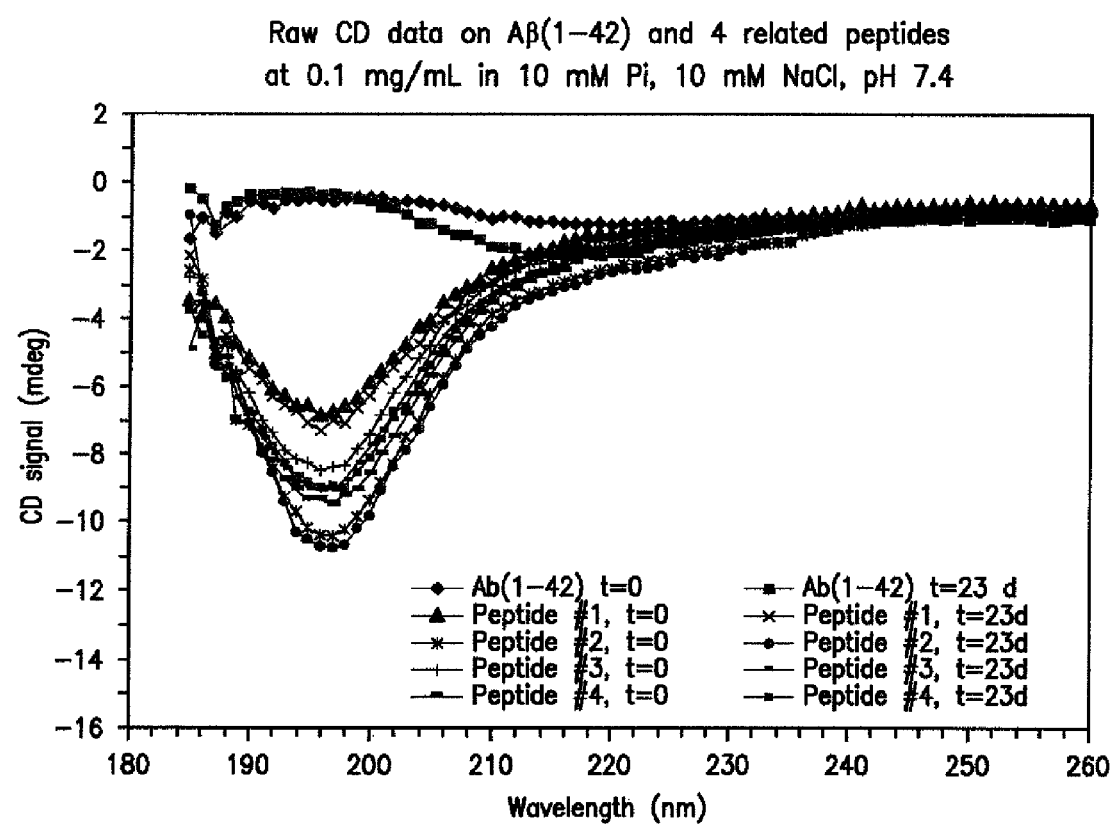
FIG. 8 shows circular dichroism analysis.
Figure 9A:
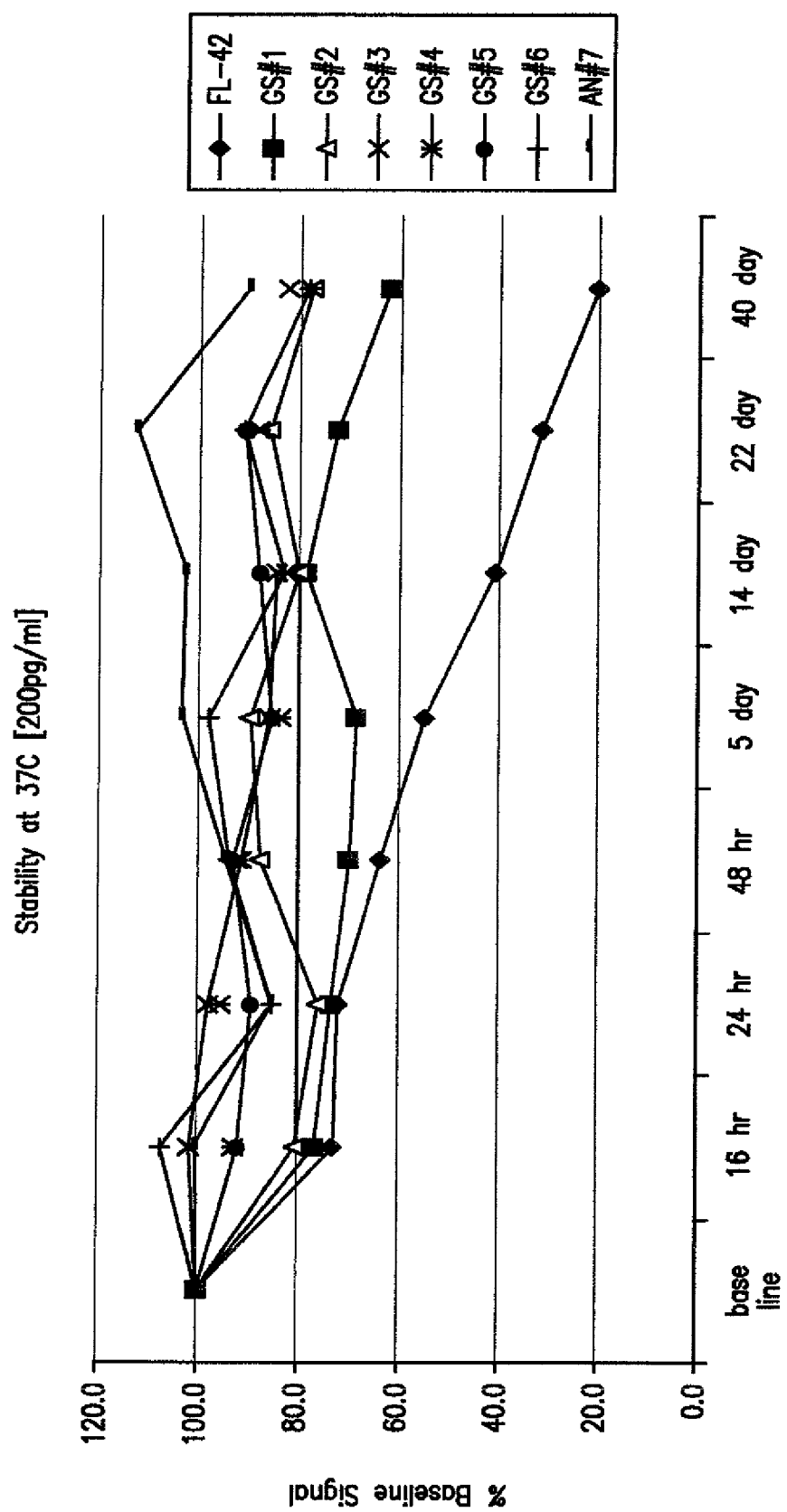
FIGS. 9A-F show peptide stability data. The full length Aβ$_{42}$ and seven modified peptides were subjected to stability studies at different temperatures for up to 40 days (FIGS. 9A-9F).
Figure 9B:
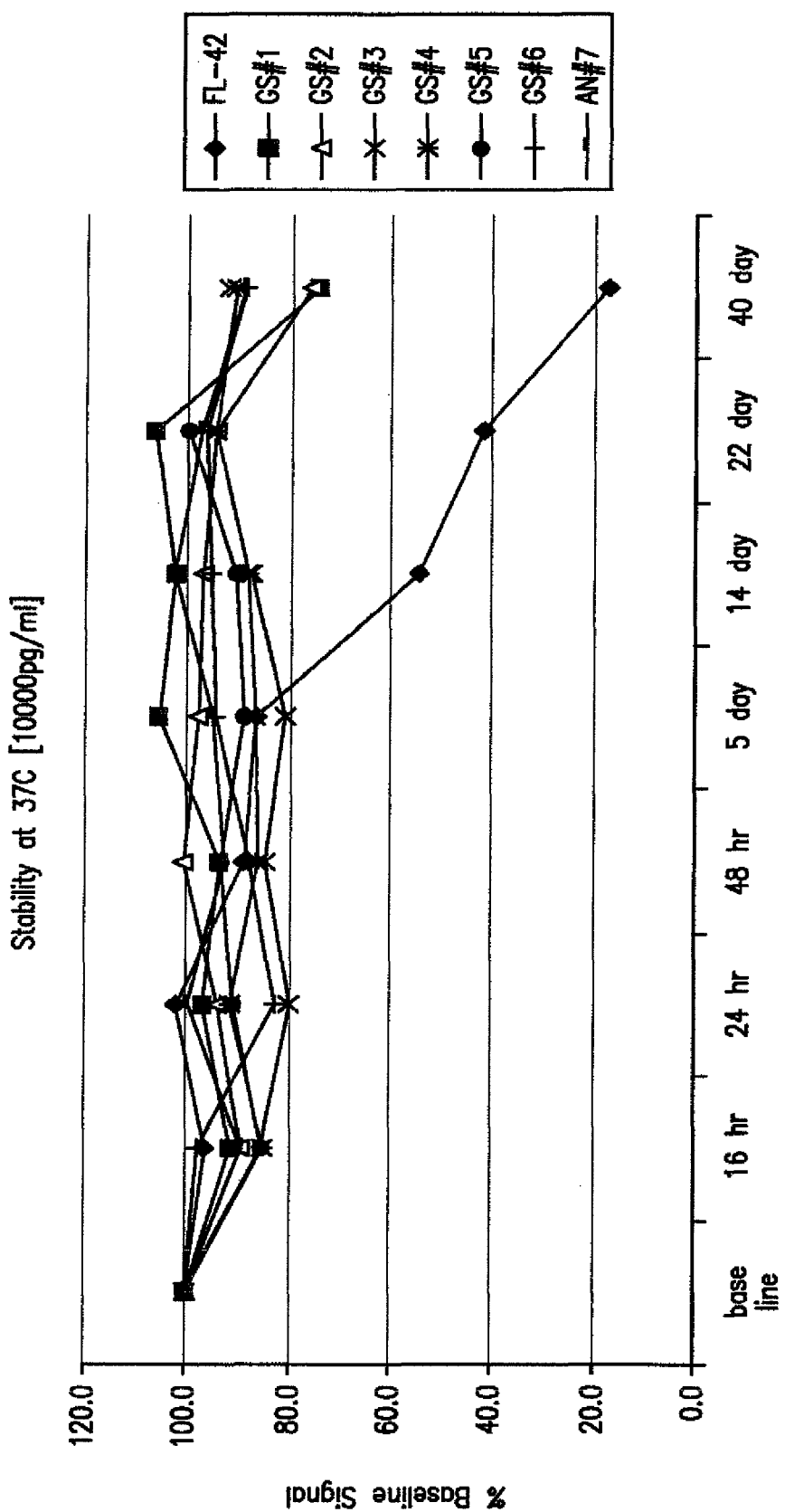
Figure 9C:
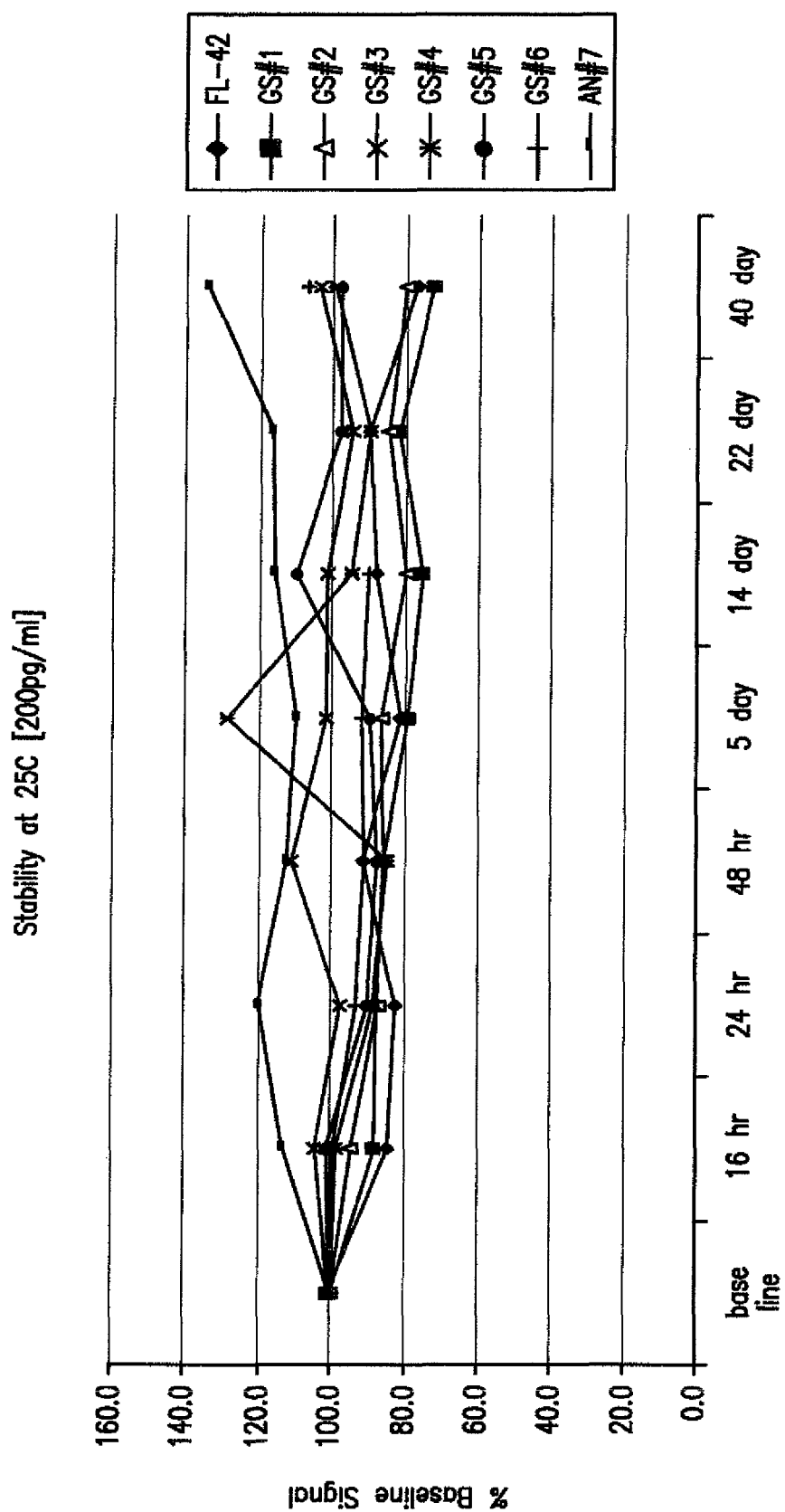
Figure 9D:
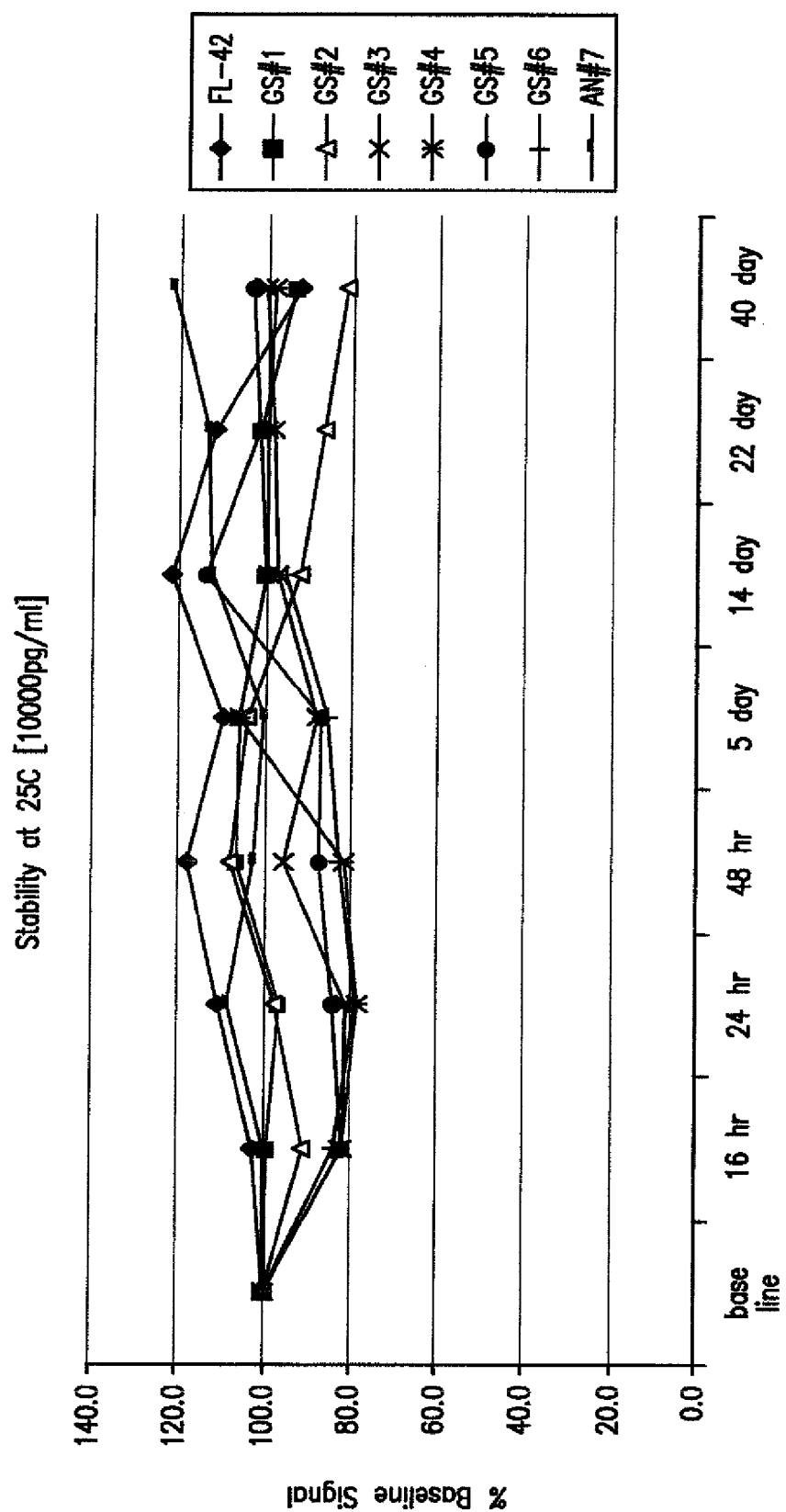
Figure 9E:
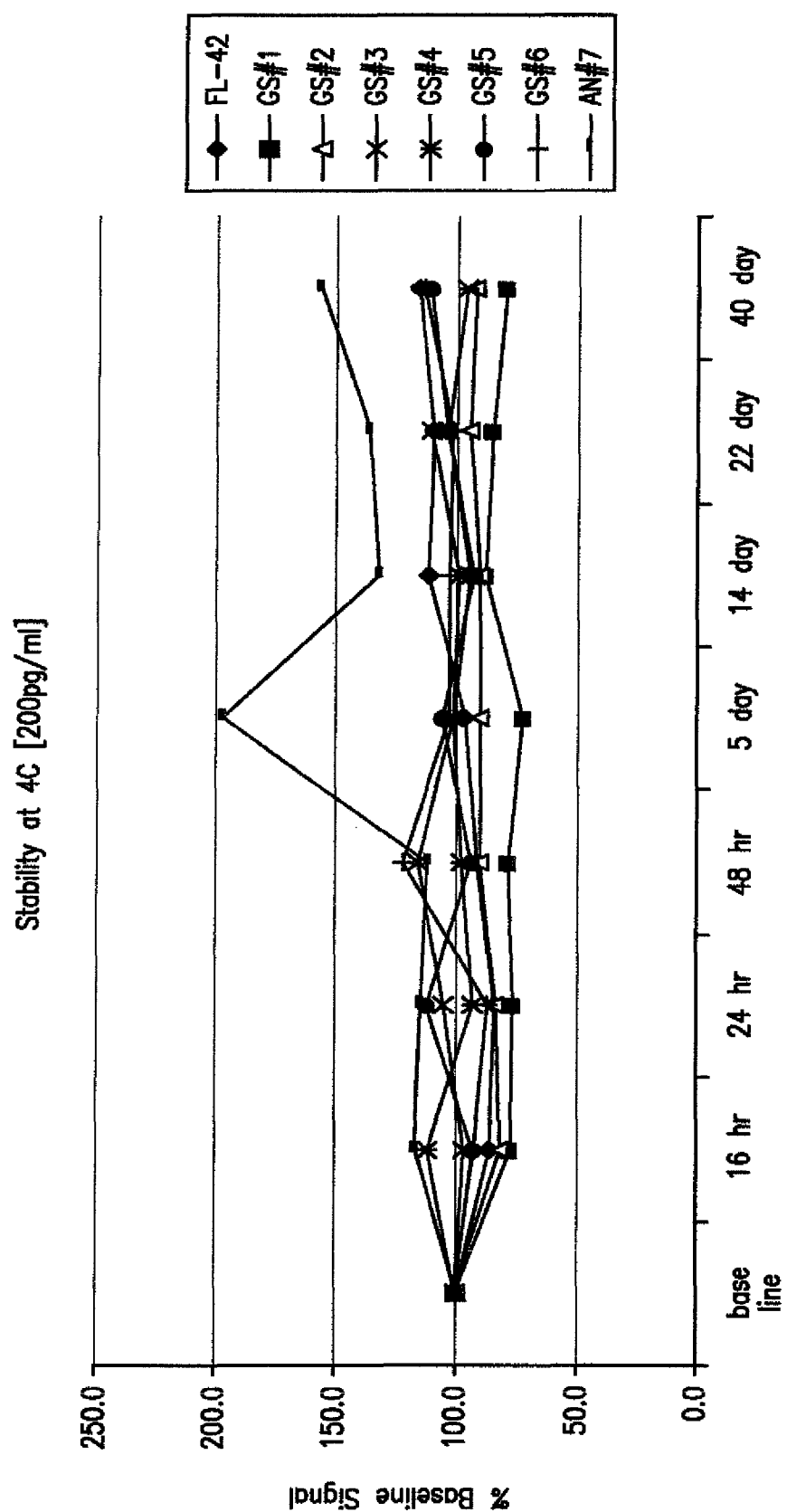
Figure 9F:
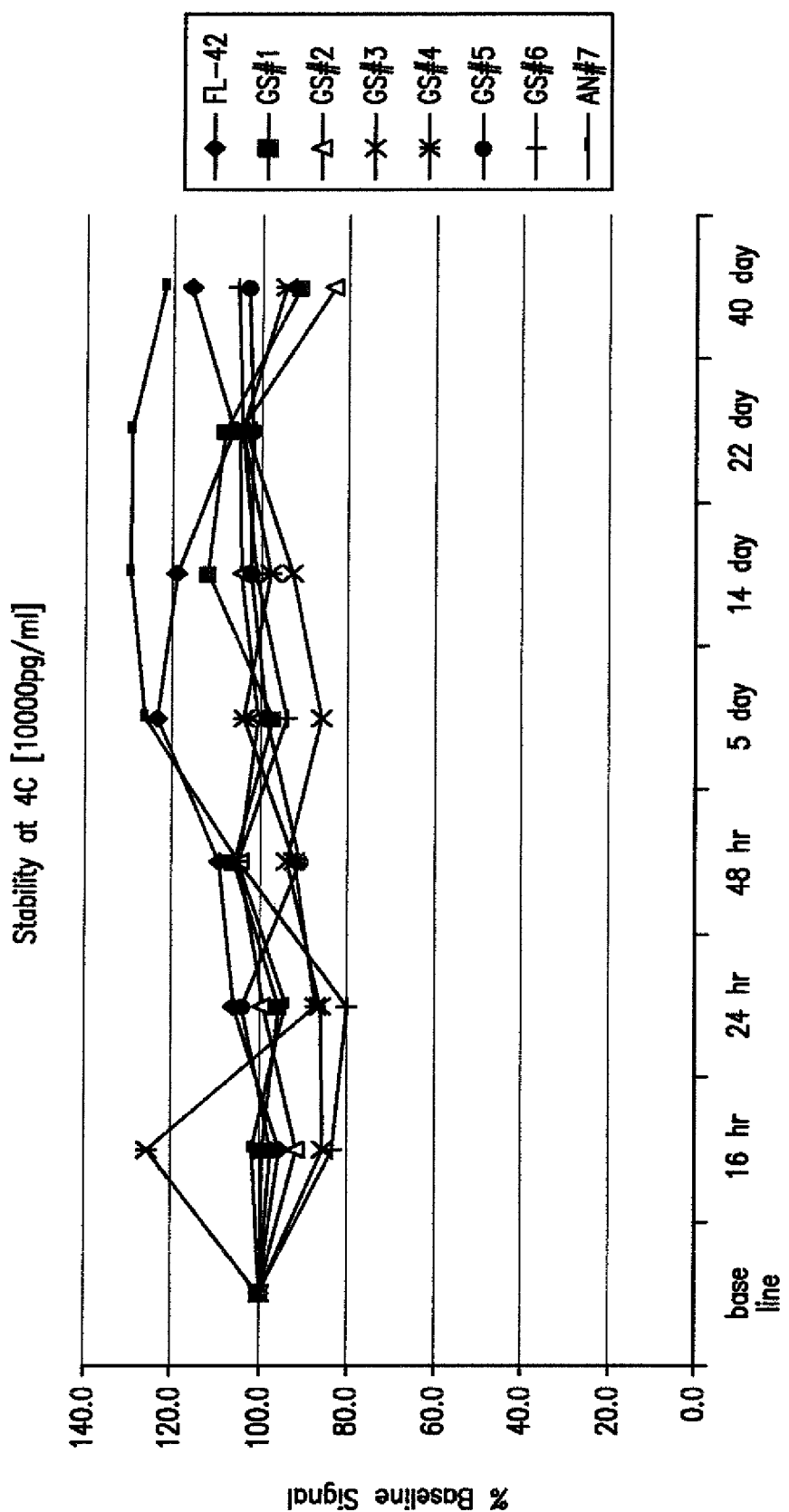
Figure 10A:
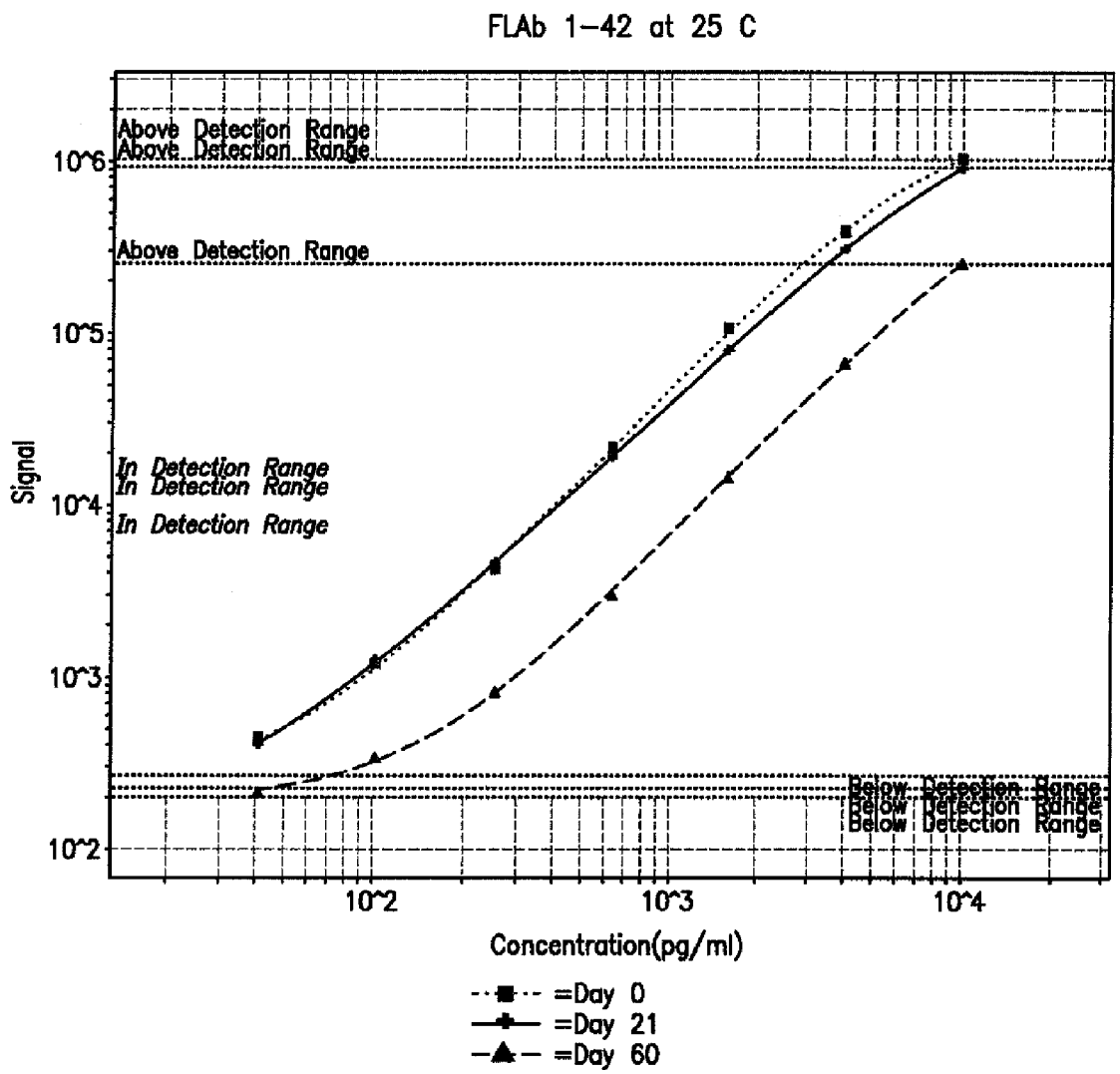
FIGS. 10A-I show a standard curve comparison between full length Aβ$_{42}$ and seven modified peptides.
Figure 10B:
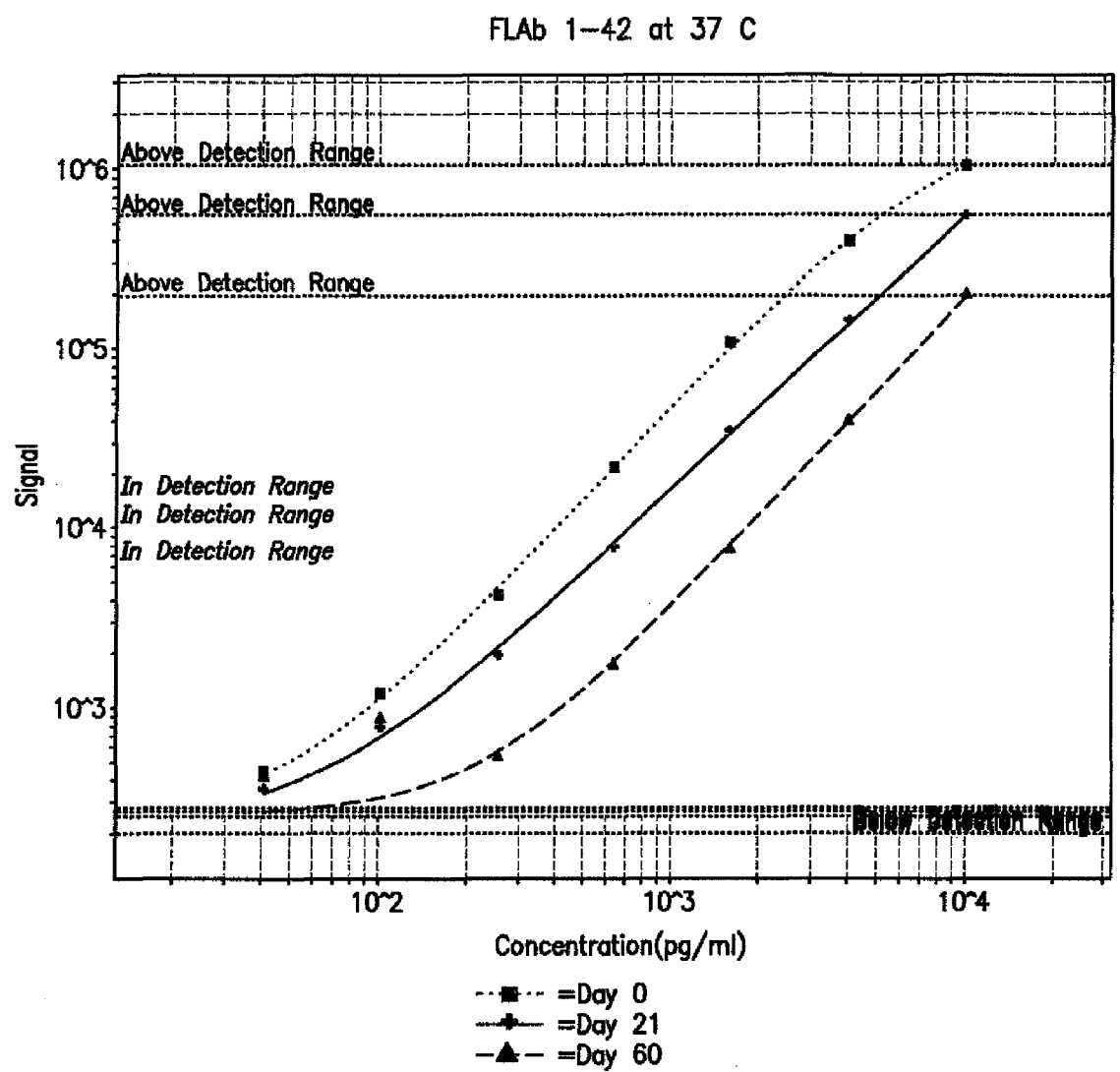
Figure 10C:
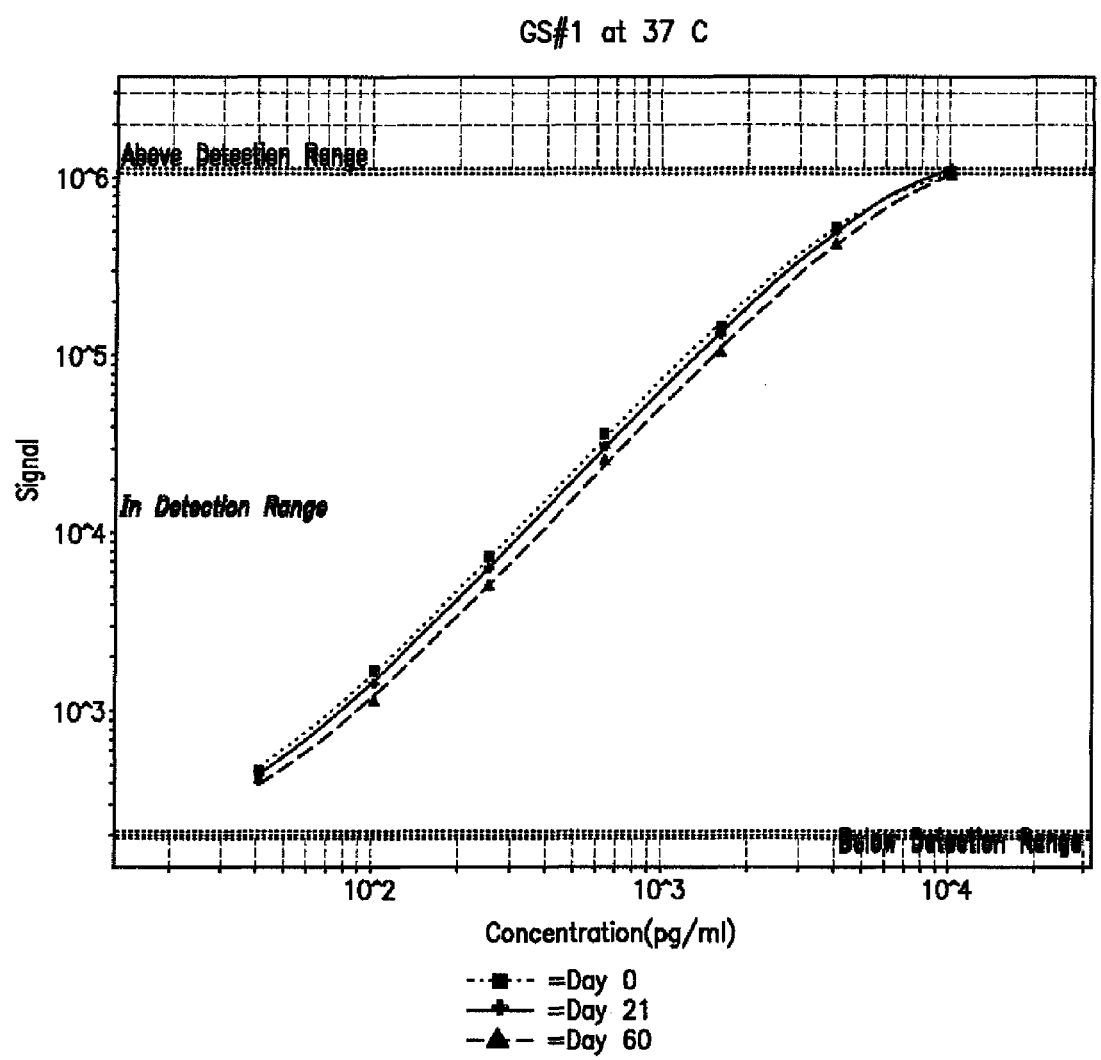
Figure 10D:
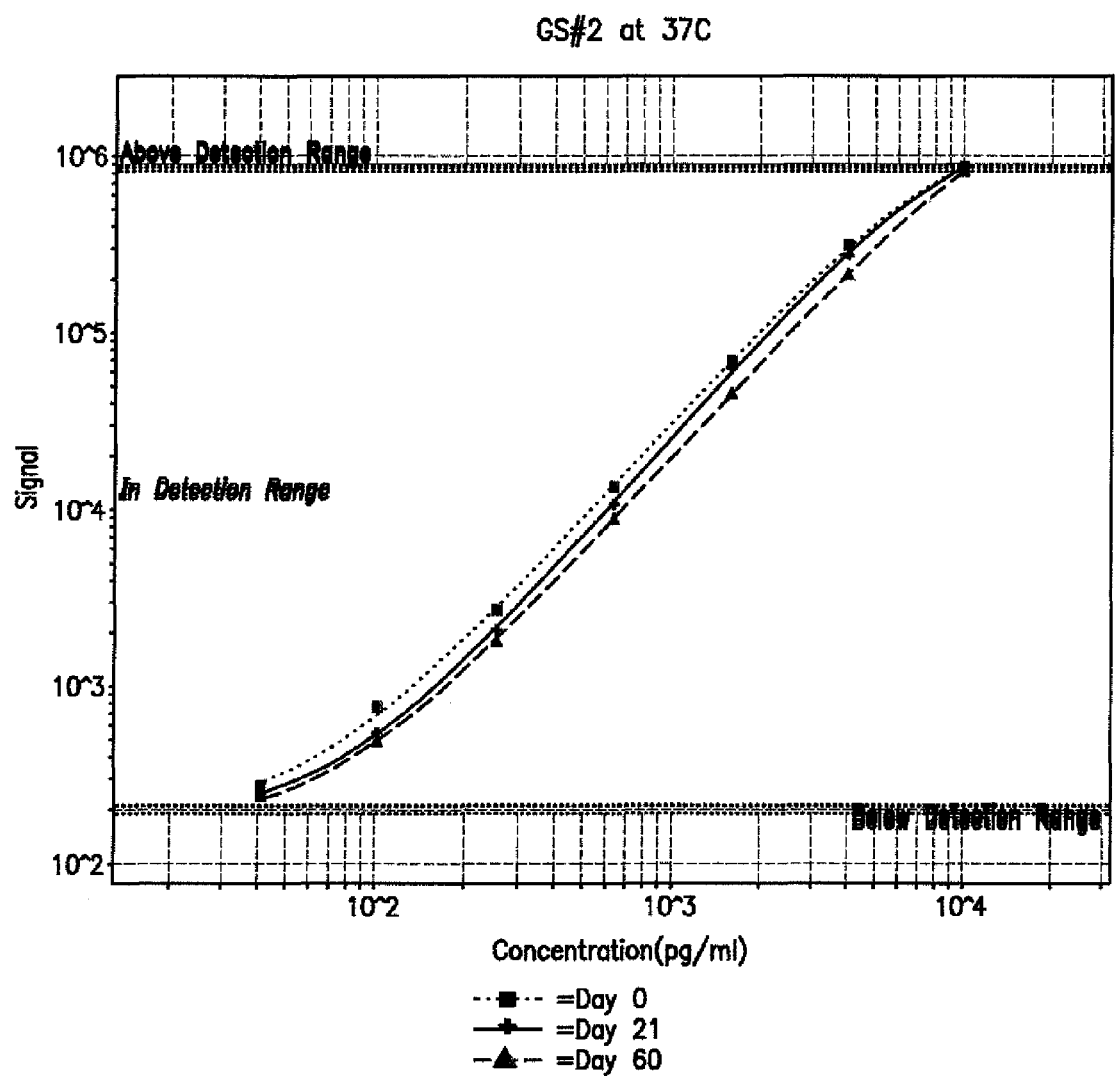
Figure 10E:
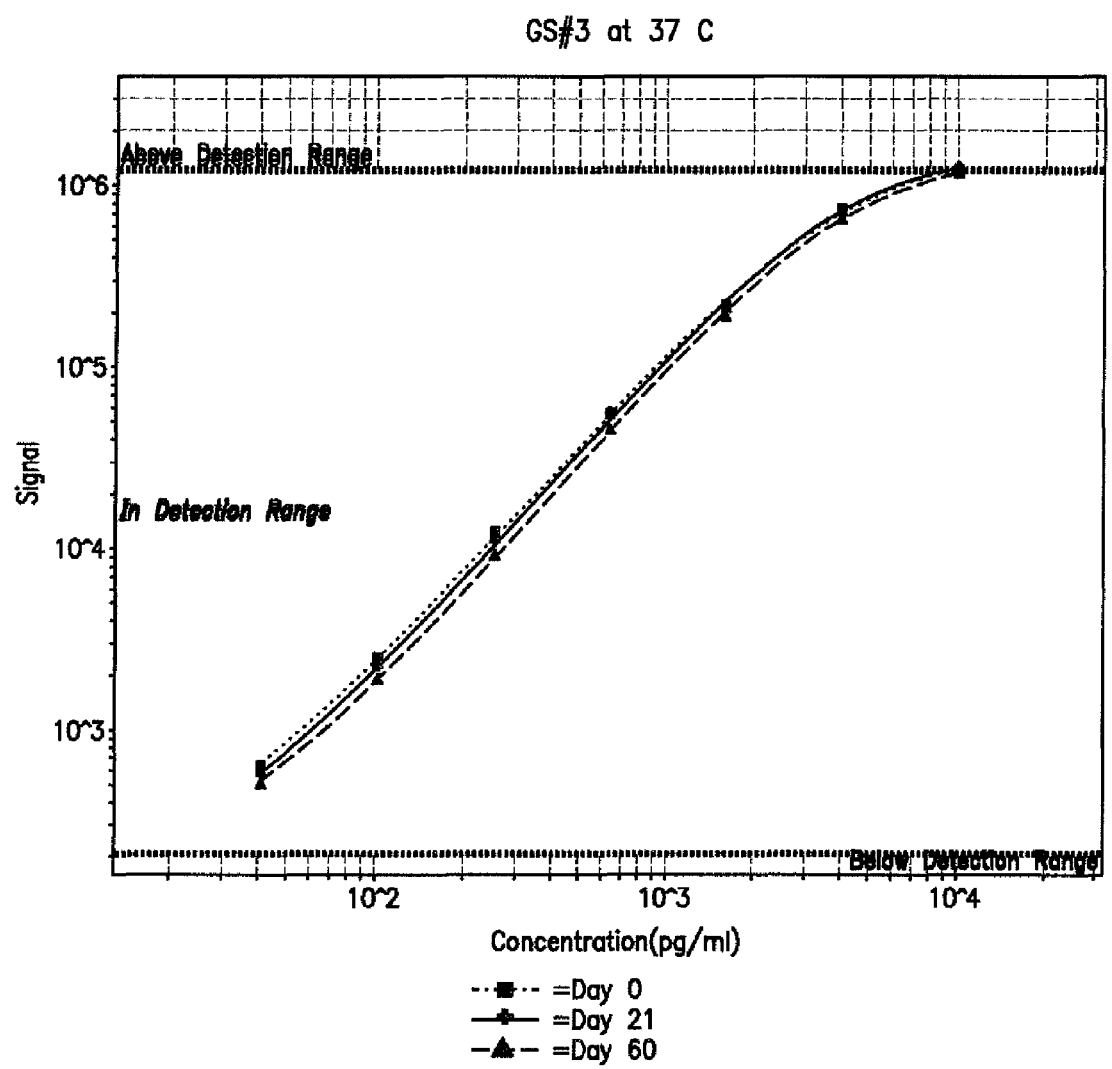
Figure 10F:
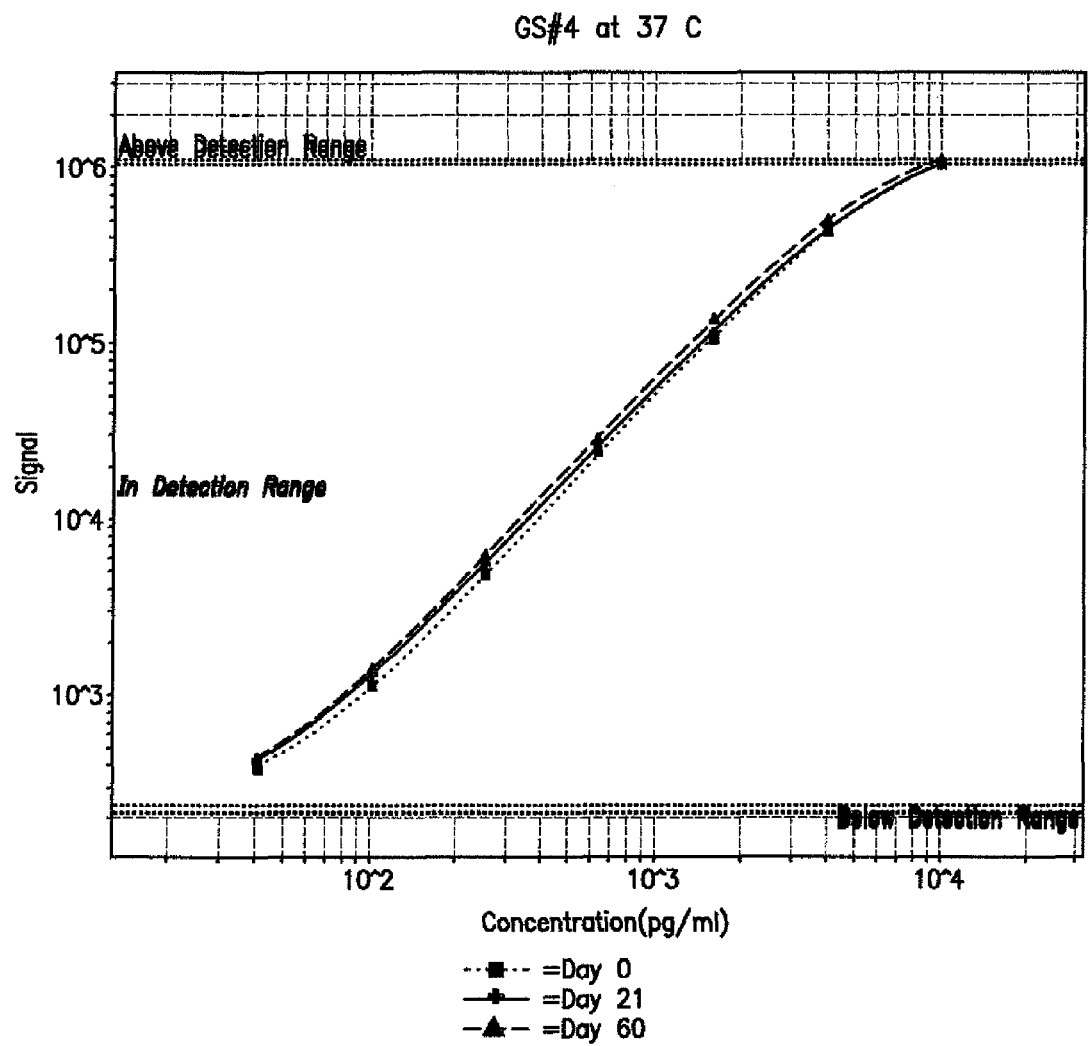
Figure 10G:
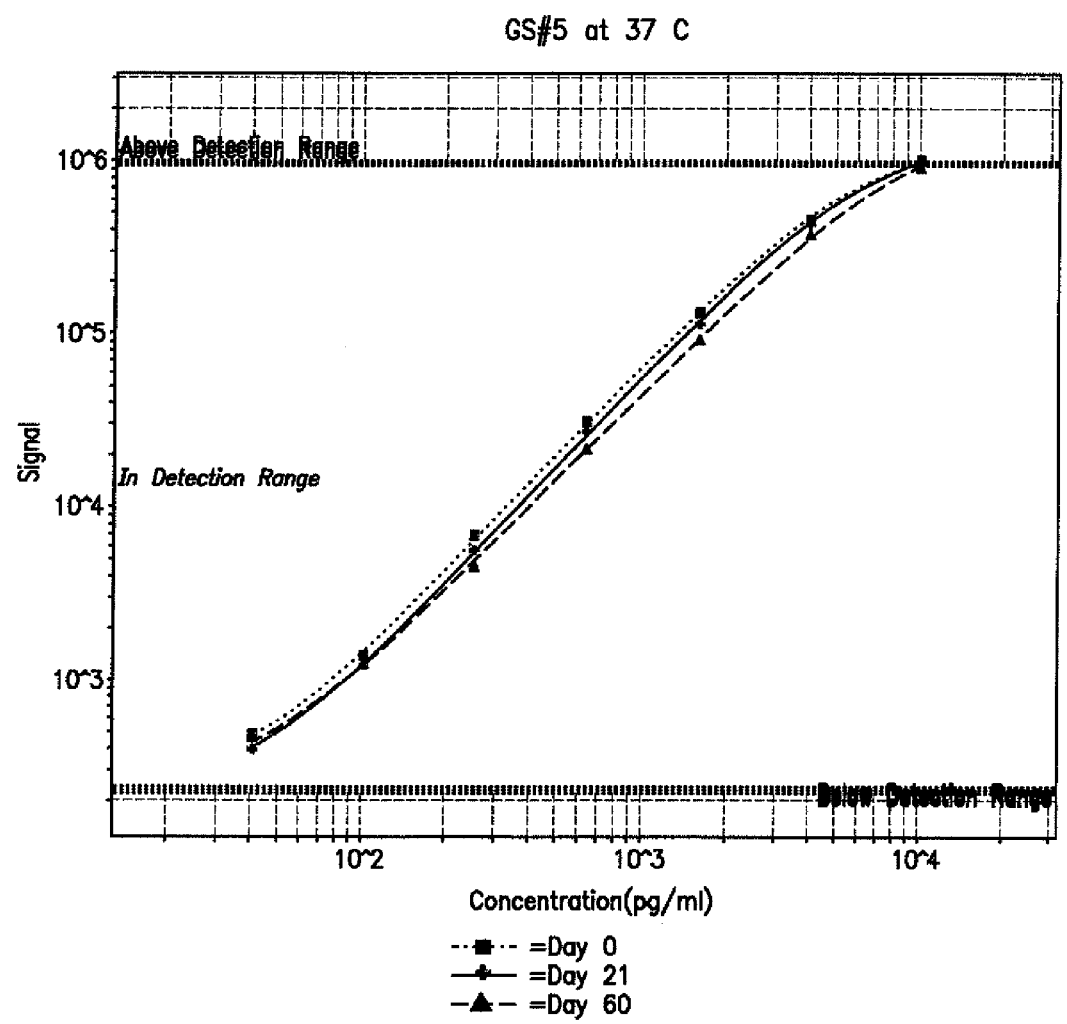
Figure 10H:
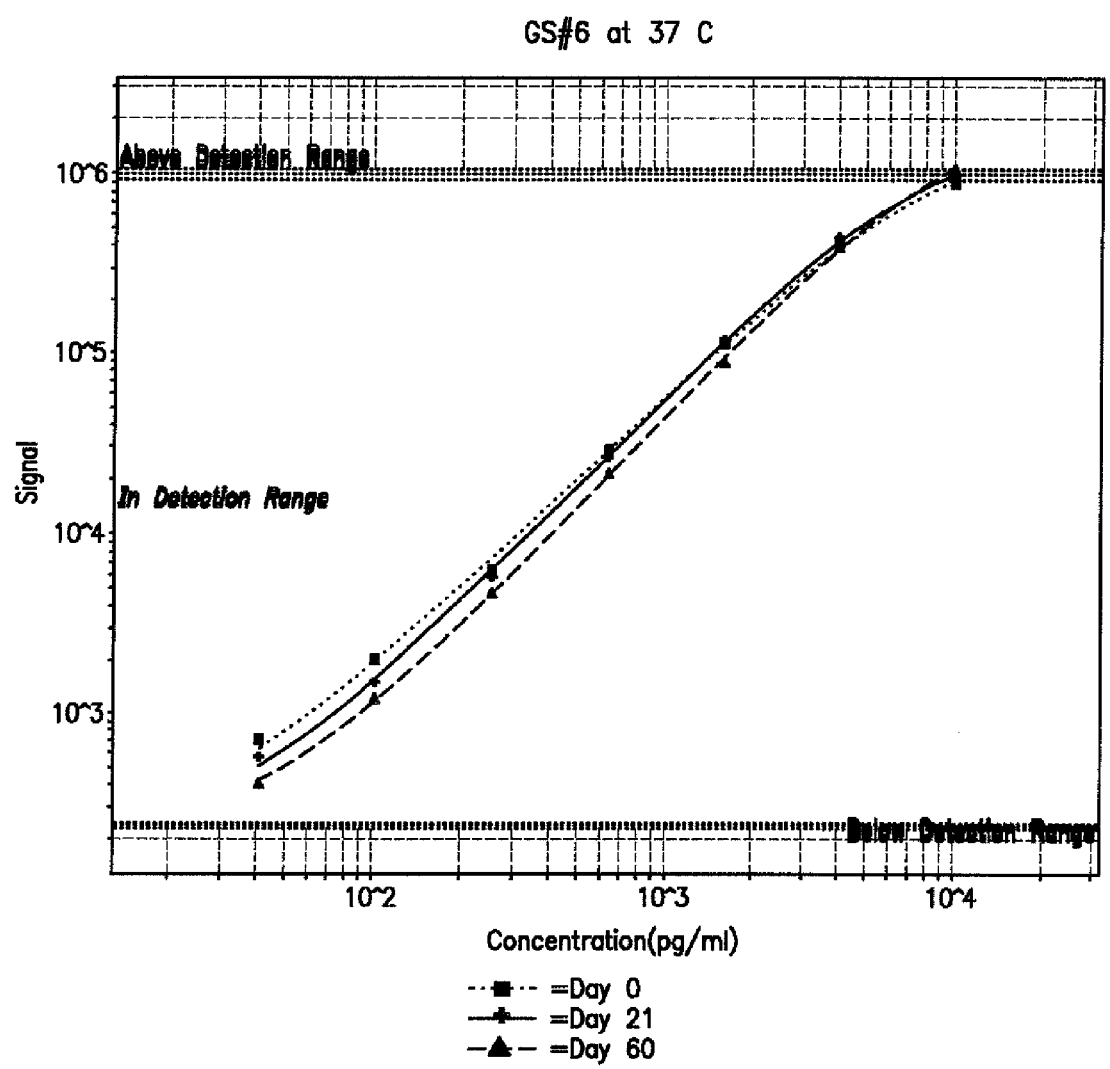
Figure 10I:
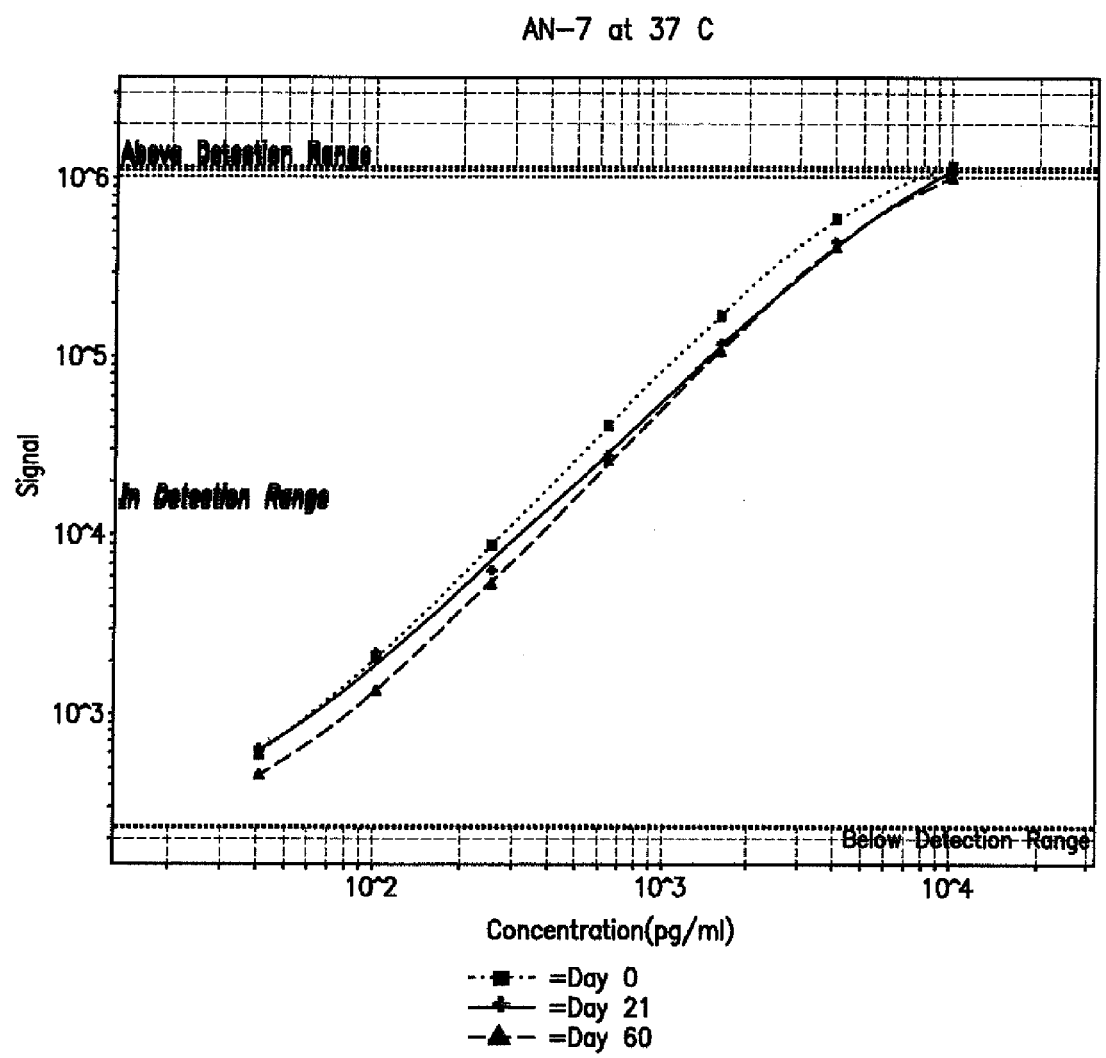

FIG. 8 shows the circular dichroism analysis. Circular dichroism analysis was performed on the full length $A\beta_{42}$ and four representative peptides to determine the order and secondary structures of these peptides. As shown in FIG. 8, the full length peptide shows more of an ordered structure than the other peptides. The four representative peptides contain an unordered CD spectra when compared to the full length peptide. These data suggest that the modified peptides do not aggregate or form any higher order structures unlike that of the full length peptide.

MSD ELISA

Biotin labeled anti-C-terminal $A\beta_{42}$ antibody (565-20 μg/ml) was immobilized to a 96 well MSD streptavidin coated plate by adding 30 μl/well. The plate was then covered and incubated overnight at 25° C., shaking at 500 rpm. The plates were then washed 3× with 300 μl/well of wash buffer (R & D system cat# WA126). After washing, 225 μl/well of blocking buffer (1% BSA+0.1% Tween-20 in PBS) was added to the plate and incubated for 30 minutes at room temperature, shaking at 500 rpm. Once the blocking step was done, the plates were washed as described previously. Reference standard $A\beta_{42}$ peptides (full length or modified peptides) were added to the wells. $A\beta_{42}$ peptides were captured by the immobilized capture antibody. A second ruthenium tagged (Ru) antibody to the N-terminus of $A\beta_{42}$ (26D6) was added thereby completing the sandwich. The complex was detected using an MSD sector 6000 instrument using ECL. The raw fluorescence units (RFU) measured by the instrument were fit to a 4-parameter logistic model to create a standard curve.

FIGS. 9A-F show peptide stability data. The full length $A\beta_{42}$ and seven modified peptides were subjected to stability studies at different temperatures for up to 40 days (FIGS. 9A-9F). These peptides were kept at 4° C., 25° C., and 37° C. for the specified length of time and then frozen until the assay was run. Peptides were then collected and run on an MSD Elisa format. Results are shown as a percent of the baseline signal for each peptide measured at time zero. Indeed, short term incubation at 37° C. has been used to estimate the long term stability of molecules at 4° C. and room temperature (Anderson et al, Clinical Chemistry, 37(3): 398-402 (1991)). Therefore, incubation of the peptides at 37° C. for short term analysis can be used to assess the long term stability of the peptides. As shown in FIGS. 9A-F, the full length $A\beta_{42}$ peptide signal drops dramatically starting at 16 hr incubation at 37° C. In contrast, the modified peptides remain stable at all temperatures measured. This data would suggest that these modified peptides are more stable than the full length $A\beta_{42}$.

FIGS. 10A-10I show the full length $A\beta_{42}$ and seven modified peptides were subjected to stability studies at different temperatures for up to 60 days. These peptides were kept at 25° C. and 37° C. for the specified length of time and then frozen until the assay was run. Peptides were then collected and run on an MSD Elisa format. Results are shown as a standard curve, plotting signal versus peptide concentration. As shown in FIGS. 10A-I, the full length peptide gave decreasing standard curves at 25° C. and 37° C. In comparison, all seven peptides analyzed gave similar curves across all time points and temperature ranges (only 37° C. shown). The results suggest that the modified peptides will give a more consistent signal than the full length $A\beta_{42}$ peptide when used as a standard for assay reproducibility.

Figure 11:
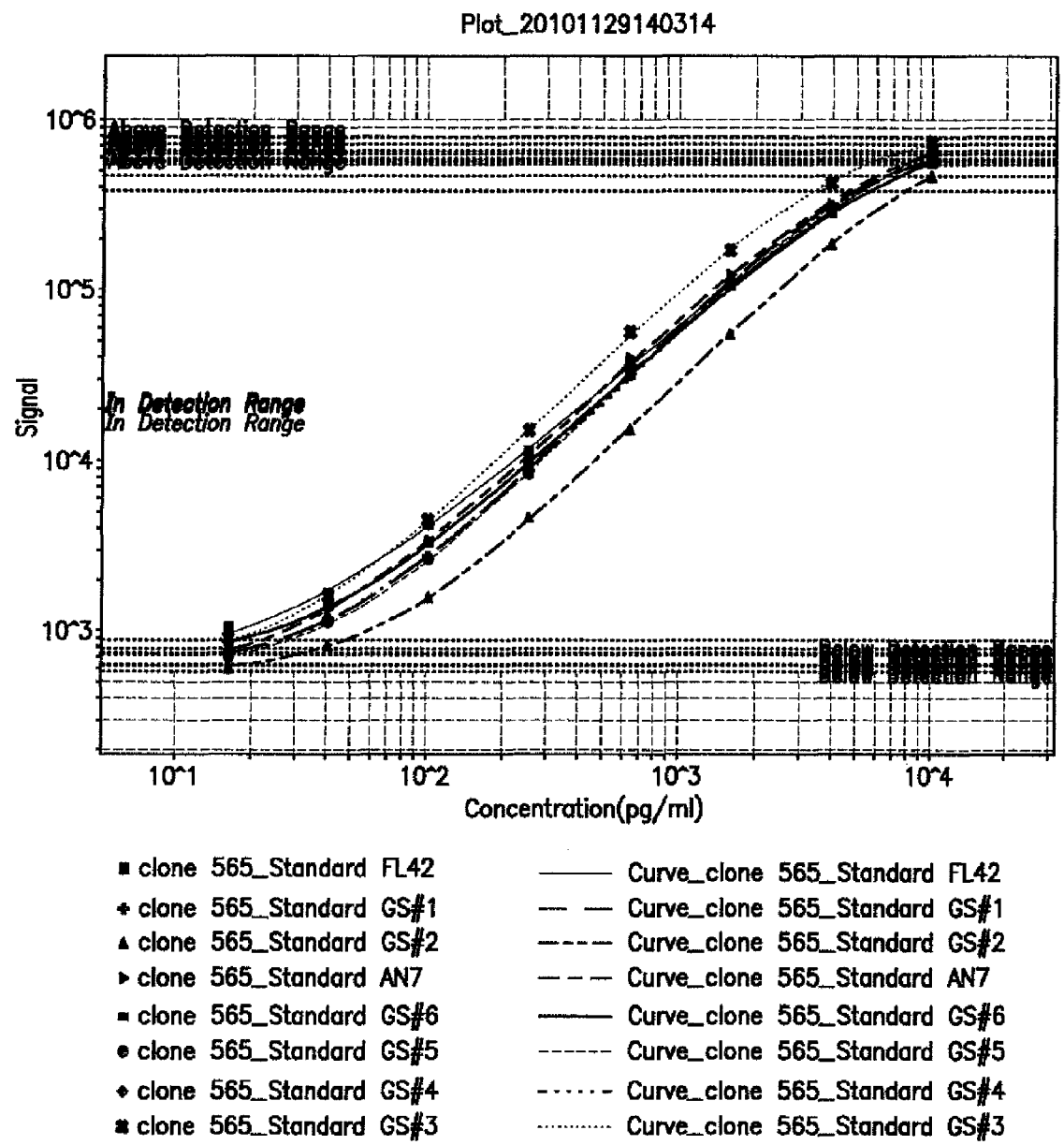
FIG. 11 shows the standard curve analysis of full length versus modified peptides.

FIG. 11 shows the standard curve analysis of full length versus modified peptides. Full length $A\beta_{42}$ and seven modified peptides were diluted out for an eight point calibration curve and ran on the MSD Elisa format. As shown in FIG. 11, all of the peptides produced almost identical standard curves. This result suggests that the modified peptides can be used in the place of the full length peptide for the calculation of Aβ in sample matrixes.

Figure 12:
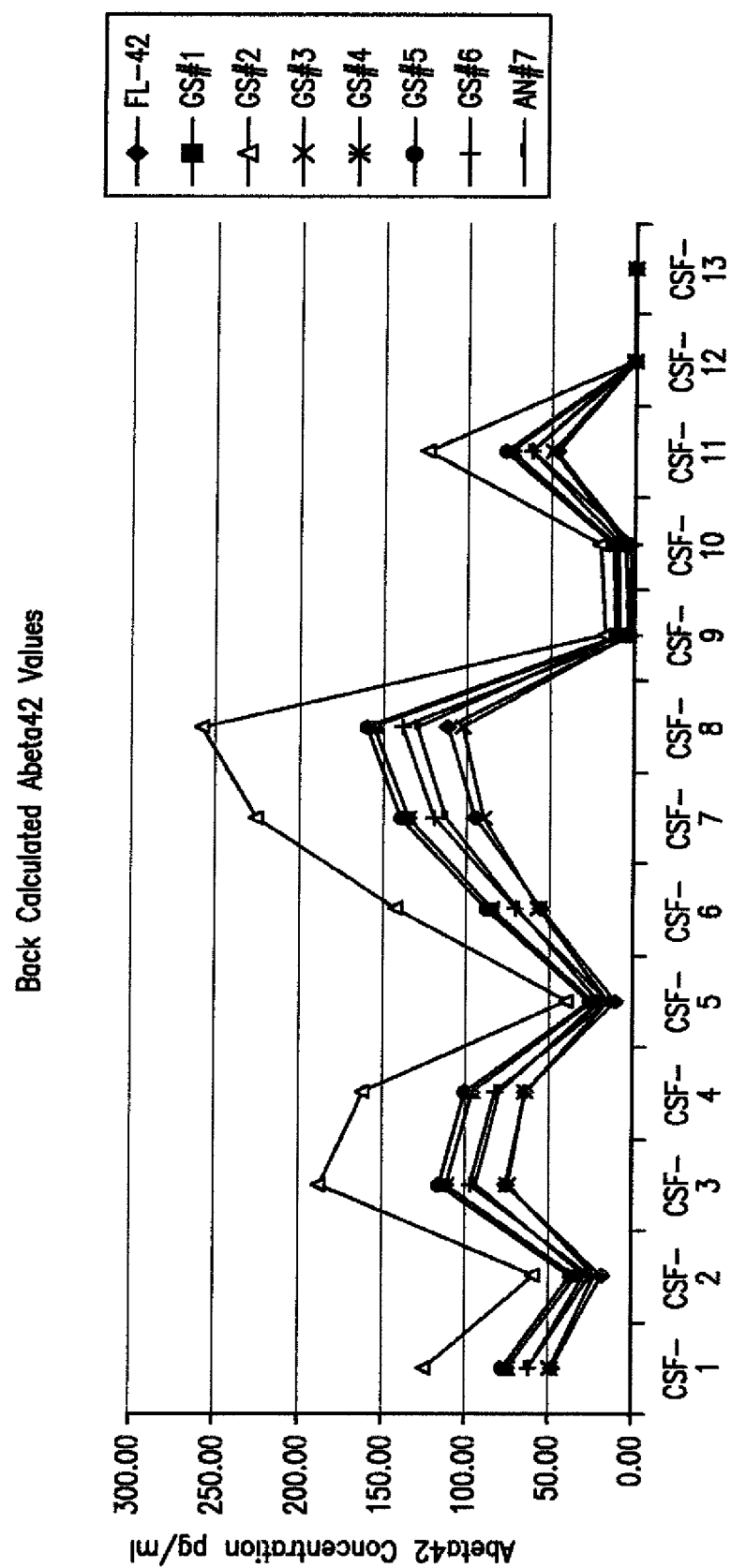
FIG. 12 shows a CSF sample analysis using full length versus modified peptides.

FIG. 12 shows a CSF sample analysis using full length versus modified peptides. Full length $A\beta_{42}$ and seven modified peptides were diluted out for an eight point calibration curve and ran on the MSD Elisa format with 13 CSF samples. The concentration of Aβ in each CSF sample was calculated based on the standard curve for each peptide. As shown in FIG. 12, the back calculated Aβ concentrations in the CSF samples were equivalent and was independent of which Aβ peptide used for the standard curve. This suggests that these modified peptides can be used in place of the full length $A\beta_{42}$ peptide in these assays without affecting the calculations of the Aβ levels.

We claims:

1. An isolated modified Aβ$_{42}$ peptide consisting of an amino acid sequence selected from the group consisting of SEQ ID NO: 6, SEQ ID NO: 12 and SEQ ID NO:13, wherein the peptide is a non-aggregating peptide.

2. The isolated, modified peptide of claim 1, wherein peptide is used as a reference standard in an immunoassay.

3. The peptide of claim 2, wherein the immunoassay is selected from the group consisting of a sandwich immunoassay, a single antibody assay, a double sandwich immunoassay and a competition assay.

4. A kit for conducting an immunoassay to detect Aβ$_{42}$ peptide in a sample, the kit comprising: the peptide of claim 1, written instructions and a container containing the components.

* * * * *

```
                        SEQUENCE LISTING

<160> NUMBER OF SEQ ID NOS: 27

<210> SEQ ID NO 1
<211> LENGTH: 42
<212> TYPE: PRT
<213> ORGANISM: Artificial Sequence
<220> FEATURE:
<223> OTHER INFORMATION: Peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 21
<212> TYPE: PRT
<213> ORGANISM: Artificial Sequence
<220> FEATURE:
<223> OTHER INFORMATION: Modified Peptide

<400> SEQUENCE: 2

Asp Ala Glu Phe Arg His Asp Ser Gly Tyr Glu Val His Met Val Gly
1               5                   10                  15

Gly Val Val Ile Ala
            20

<210> SEQ ID NO 3
<211> LENGTH: 22
<212> TYPE: PRT
<213> ORGANISM: Artificial Sequence
<220> FEATURE:
<223> OTHER INFORMATION: Modified Peptide

<400> SEQUENCE: 3

Asp Ala Glu Phe Arg His Asp Ser Gly Tyr Glu Val His His Gln Lys
1               5                   10                  15

Gly Gly Val Val Ile Ala
            20

<210> SEQ ID NO 4
<211> LENGTH: 27
<212> TYPE: PRT
<213> ORGANISM: Artificial Sequence
<220> FEATURE:
<223> OTHER INFORMATION: Modified Peptide

<400> SEQUENCE: 4

Asp Ala Glu Phe Arg His Asp Ser Gly Tyr Glu Val His His Gln Lys
1               5                   10                  15

Ile Gly Leu Met Val Gly Gly Val Val Ile Ala
            20                  25

<210> SEQ ID NO 5
<211> LENGTH: 26
<212> TYPE: PRT
```

```
<213> ORGANISM: Artificial Sequence
<220> FEATURE:
<223> OTHER INFORMATION: Modified Peptide

<400> SEQUENCE: 5

Asp Ala Glu Phe Arg His Asp Ser Gly Tyr Glu Val His His Gln Lys
1               5                   10                  15

Glu Glu Arg Pro Gly Gly Val Val Ile Ala
            20                  25

<210> SEQ ID NO 6
<211> LENGTH: 31
<212> TYPE: PRT
<213> ORGANISM: Artificial Sequence
<220> FEATURE:
<223> OTHER INFORMATION: Modified Peptide

<400> SEQUENCE: 6

Asp Ala Glu Phe Arg His Asp Ser Gly Tyr Glu Val His His Gln Lys
1               5                   10                  15

Glu Glu Arg Pro Ile Gly Leu Met Val Gly Gly Val Val Ile Ala
            20                  25                  30

<210> SEQ ID NO 7
<211> LENGTH: 28
<212> TYPE: PRT
<213> ORGANISM: Artificial Sequence
<220> FEATURE:
<223> OTHER INFORMATION: Modified Peptide

<400> SEQUENCE: 7

Asp Ala Glu Phe Arg His Asp Ser Gly Tyr Glu Val His His Gln Lys
1               5                   10                  15

Asp Arg Glu Glu Arg Pro Gly Gly Val Val Ile Ala
            20                  25

<210> SEQ ID NO 8
<211> LENGTH: 33
<212> TYPE: PRT
<213> ORGANISM: Artificial Sequence
<220> FEATURE:
<223> OTHER INFORMATION: Modified Peptide

<400> SEQUENCE: 8

Asp Ala Glu Phe Arg His Asp Ser Gly Tyr Glu Val His His Gln Lys
1               5                   10                  15

Asp Arg Glu Pro Asn Arg Ile Gly Leu Met Val Gly Gly Val Val Ile
            20                  25                  30

Ala

<210> SEQ ID NO 9
<211> LENGTH: 23
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (17)..(36)
<223> OTHER INFORMATION: Xaa represents up to 20 Lys residues located
      between Lys at position 16 and Gly at position 18

<400> SEQUENCE: 9

Asp Ala Glu Phe Arg His Asp Ser Gly Tyr Glu Val His His Gln Lys
1               5                   10                  15
```

```
Xaa Gly Gly Val Val Ile Ala
            20

<210> SEQ ID NO 10
<211> LENGTH: 23
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (17)..(36)
<223> OTHER INFORMATION: Xaa represents up to 20 Glu acid residues
      located between Lys at position 16 and Gly at position 18

<400> SEQUENCE: 10

Asp Ala Glu Phe Arg His Asp Ser Gly Tyr Glu Val His His Gln Lys
1               5                   10                  15

Xaa Gly Gly Val Val Ile Ala
            20

<210> SEQ ID NO 11
<211> LENGTH: 23
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (17)..(36)
<223> OTHER INFORMATION: Xaa represents up to 20 Ala residues located
      between Lys at position 16 and Gly at position 18

<400> SEQUENCE: 11

Asp Ala Glu Phe Arg His Asp Ser Gly Tyr Glu Val His His Gln Lys
1               5                   10                  15

Xaa Gly Gly Val Val Ile Ala
            20

<210> SEQ ID NO 12
<211> LENGTH: 22
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (17)..(36)
<223> OTHER INFORMATION: Sequence comprises a PEG(20-ATOMS)3 linker
      located between Lys located at position 16 and the Gly located at
      position 17

<400> SEQUENCE: 12

Asp Ala Glu Phe Arg His Asp Ser Gly Tyr Glu Val His His Gln Lys
1               5                   10                  15

Gly Gly Val Val Ile Ala
            20

<210> SEQ ID NO 13
<211> LENGTH: 24
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (17)..(34)
<223> OTHER INFORMATION: Sequence comprises a PEG(9-ATOMS)6 linker
``` located between Lys at position 16 and Met at position 17

<400> SEQUENCE: 13

Asp Ala Glu Phe Arg His Asp Ser Gly Tyr Glu Val His His Gln Lys
1               5                   10                  15

Met Val Gly Gly Val Val Ile Ala
            20

<210> SEQ ID NO 14
<211> LENGTH: 27
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (17)..(31)
<223> OTHER INFORMATION: Sequence comprises a PEG(9-ATOMS)5 linker
      located between Lys at position 16 and Ile at position 17

<400> SEQUENCE: 14

Asp Ala Glu Phe Arg His Asp Ser Gly Tyr Glu Val His His Gln Lys
1               5                   10                  15

Ile Gly Leu Met Val Gly Gly Val Val Ile Ala
            20                  25

<210> SEQ ID NO 15
<211> LENGTH: 40
<212> TYPE: PRT
<213> ORGANISM: Artificial Sequence
<220> FEATURE:
<223> OTHER INFORMATION: Modified Peptide

<400> SEQUENCE: 15

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 16
<211> LENGTH: 6
<212> TYPE: PRT
<213> ORGANISM: Artificial Sequence
<220> FEATURE:
<223> OTHER INFORMATION: Modified Peptide

<400> SEQUENCE: 16

Asp Arg Glu Pro Asn Arg
1               5

<210> SEQ ID NO 17
<211> LENGTH: 38
<212> TYPE: PRT
<213> ORGANISM: Artificial Sequence
<220> FEATURE:
<223> OTHER INFORMATION: Modified Peptide

<400> SEQUENCE: 17

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

```
Gly Leu Met Val Gly Gly
        35
```

<210> SEQ ID NO 18
<211> LENGTH: 5
<212> TYPE: PRT
<213> ORGANISM: Artificial Sequence
<220> FEATURE:
<223> OTHER INFORMATION: Modified Peptide

<400> SEQUENCE: 18

```
Lys Leu Val Phe Phe
1               5
```

<210> SEQ ID NO 19
<211> LENGTH: 63
<212> TYPE: PRT
<213> ORGANISM: Artificial Sequence
<220> FEATURE:
<223> OTHER INFORMATION: Modified Peptide

<400> SEQUENCE: 19

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Asp Ala Glu Phe Arg His
        35                  40                  45

Asp Ser Gly Tyr Glu Val His Met Val Gly Gly Val Val Ile Ala
    50                  55                  60
```

<210> SEQ ID NO 20
<211> LENGTH: 441
<212> TYPE: PRT
<213> ORGANISM: Artificial Sequence
<220> FEATURE:
<223> OTHER INFORMATION: Modified Peptide

<400> SEQUENCE: 20

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
```

```
                        165                 170                 175
Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 21
<211> LENGTH: 24
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (12)..(13)
<223> OTHER INFORMATION: Sequence comprises a generic linker located
      between Leu at position 12 and Gly at position 13

<400> SEQUENCE: 21

Glu Val Met Glu Asp His Ala Gly Thr Tyr Gly Leu Gly Ala Ala Pro
1               5                   10                  15

Pro Gly Gln Lys Gly Gln Ala Asn
            20

<210> SEQ ID NO 22
<211> LENGTH: 22
<212> TYPE: PRT
<213> ORGANISM: Artificial Sequence
```

```
<220> FEATURE:
<223> OTHER INFORMATION: Modified Peptide
<220> FEATURE:
<221> NAME/KEY: MISC_FEATURE
<222> LOCATION: (12)..(13)
<223> OTHER INFORMATION: Sequence comprises a generic linker located
      between Leu at position 12 and Ser at position 13

<400> SEQUENCE: 22

Glu Val Met Glu Asp His Ala Gly Thr Tyr Gly Leu Ser Gly Asp Arg
1               5                   10                  15

Ser Gly Tyr Ser Ser Pro
            20

<210> SEQ ID NO 23
<211> LENGTH: 32
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (12)..(13)
<223> OTHER INFORMATION: Sequence comprises a generic linker located
      between Asn at position 12 and Ile at position 13
<220> FEATURE:
<221> NAME/KEY: MISC_FEATURE
<222> LOCATION: (23)..(23)
<223> OTHER INFORMATION: Sequence comprises a phosphate at Thr at
      position 23

<400> SEQUENCE: 23

Gly Ala Ala Pro Pro Gly Gln Lys Gly Gln Ala Asn Ile Pro Ala Lys
1               5                   10                  15

Thr Pro Pro Ala Pro Lys Thr Pro Pro Ser Ser Gly Glu Pro Pro Lys
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (12)..(13)
<223> OTHER INFORMATION: Sequence comprise a generic linker located
      between Asn at position 12 and Arg at position 13
<220> FEATURE:
<221> NAME/KEY: MISC_FEATURE
<222> LOCATION: (23)..(23)
<223> OTHER INFORMATION: A phosphate at Thr at position 23

<400> SEQUENCE: 24

Gly Ala Ala Pro Pro Gly Gln Lys Gly Gln Ala Asn Arg Glu Pro Lys
1               5                   10                  15

Lys Val Ala Val Val Arg Thr Pro Pro Lys Ser Pro Ser Ser Ala Lys
            20                  25                  30

<210> SEQ ID NO 25
<211> LENGTH: 22
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (12)..(13)
<223> OTHER INFORMATION: Sequence comprises a generic linker located
      between Asn at position 12 and Ser at position 13
```

```
<400> SEQUENCE: 25

Gly Ala Ala Pro Pro Gly Gln Lys Gly Gln Ala Asn Ser Gly Asp Arg
1               5                   10                  15

Ser Gly Tyr Ser Ser Pro
            20

<210> SEQ ID NO 26
<211> LENGTH: 30
<212> TYPE: PRT
<213> ORGANISM: Artificial Sequence
<220> FEATURE:
<223> OTHER INFORMATION: Modified Peptide
<220> FEATURE:
<221> NAME/KEY: MISC_FEATURE
<222> LOCATION: (12)..(13)
<223> OTHER INFORMATION: A phosphate at Thr at position 11
<220> FEATURE:
<221> NAME/KEY: MISC_FEATURE
<222> LOCATION: (21)..(22)
<223> OTHER INFORMATION: Sequence comprises a generic linker located
      between Lys at position 21 and Ser at position 22

<400> SEQUENCE: 26

Ile Pro Ala Lys Thr Pro Pro Ala Pro Lys Thr Pro Pro Ser Ser Gly
1               5                   10                  15

Glu Pro Pro Lys Ser Gly Asp Arg Ser Gly Tyr Ser Ser Pro
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Modified peptide
<220> FEATURE:
<221> NAME/KEY: MISC_FEATURE
<222> LOCATION: (10)..(11)
<223> OTHER INFORMATION: Sequence comprises a generic linker between Pro
      at position 10 and Arg at position 11
<220> FEATURE:
<221> NAME/KEY: MISC_FEATURE
<222> LOCATION: (21)..(22)
<223> OTHER INFORMATION: A phosphate at Thr at position 21

<400> SEQUENCE: 27

Ser Gly Asp Arg Ser Gly Tyr Ser Ser Pro Arg Glu Pro Lys Lys Val
1               5                   10                  15

Ala Val Val Arg Thr Pro Pro Lys Ser Pro Ser Ser Ala Lys
            20                  25                  30
```